(12) United States Patent
Butler

(10) Patent No.: US 8,802,911 B2
(45) Date of Patent: Aug. 12, 2014

(54) PROCESS FOR ETHYLBENZENE PRODUCTION

(71) Applicant: James R. Butler, League City, TX (US)

(72) Inventor: James R. Butler, League City, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 13/868,505

(22) Filed: Apr. 23, 2013

(65) Prior Publication Data

US 2013/0231514 A1    Sep. 5, 2013

Related U.S. Application Data

(63) Continuation of application No. 12/568,007, filed on Sep. 28, 2009.

(60) Provisional application No. 61/101,610, filed on Sep. 30, 2008.

(51) Int. Cl.
*C07C 2/66*    (2006.01)

(52) U.S. Cl.
USPC ............................ 585/448; 585/449; 585/467

(58) Field of Classification Search
USPC ......................................... 585/448, 449, 467
See application file for complete search history.

(56) References Cited

U.S. PATENT DOCUMENTS

| | | | |
|---|---|---|---|
| 5,600,050 A | 2/1997 | Huang et al. | |
| 2007/0179329 A1* | 8/2007 | Clark | 585/467 |

FOREIGN PATENT DOCUMENTS

| | | |
|---|---|---|
| JP | 08040947 A | 2/1996 |
| JP | 2002532443 A | 10/2002 |
| JP | 2005519103 A | 6/2005 |
| JP | 2006502215 A | 1/2006 |
| JP | 11286460 A | 10/2009 |
| WO | 0035836 A1 | 6/2000 |
| WO | 03074452 A1 | 9/2003 |
| WO | 2004033394 A2 | 4/2004 |
| WO | 2008030723 A2 | 3/2008 |
| WO | 2008088934 A1 | 7/2008 |

OTHER PUBLICATIONS

Office Action issued in JP Patent Application No. 2011529337, dated Aug. 6, 2013 and English Translation thereof (7 pages).
Partial English translation of JP Patent Application No. 08040947, published Feb. 13, 1996 (5 pages).
English abstract of JP 11286460 from Patent Abstracts of Japan, published Oct. 19, 1999 (1 page).
Honglin Wang et al., "Surface acidity of H-beta and its catalytic activity for alkylation of benezene with propylene", Catalysis Letters, vol. 76, No. 3-4, 2001, pp. 225-229, XP002722416.
Extended Search Report for European Application No. 09818338.7-1454 mailed on Apr. 9, 2014 (5 pages).

* cited by examiner

*Primary Examiner* — Thuan D Dang

(57) ABSTRACT

A method of producing an alkylaromatic by the alkylation of an aromatic with an alkylating agent, such as producing ethylbenzene by an alkylation reaction of benzene, is disclosed. The method includes using an H-beta catalyst to minimize process upsets due to alkylation catalyst deactivation and the resulting catalyst regeneration or replacement. The H-beta catalyst can be used in a preliminary alkylation reactor that is located upstream of the primary alkylation reactor. The H-beta catalyst used in a preliminary alkylation reactor can reduce the deactivation of the catalyst in the primary alkylation reactor.

31 Claims, 5 Drawing Sheets

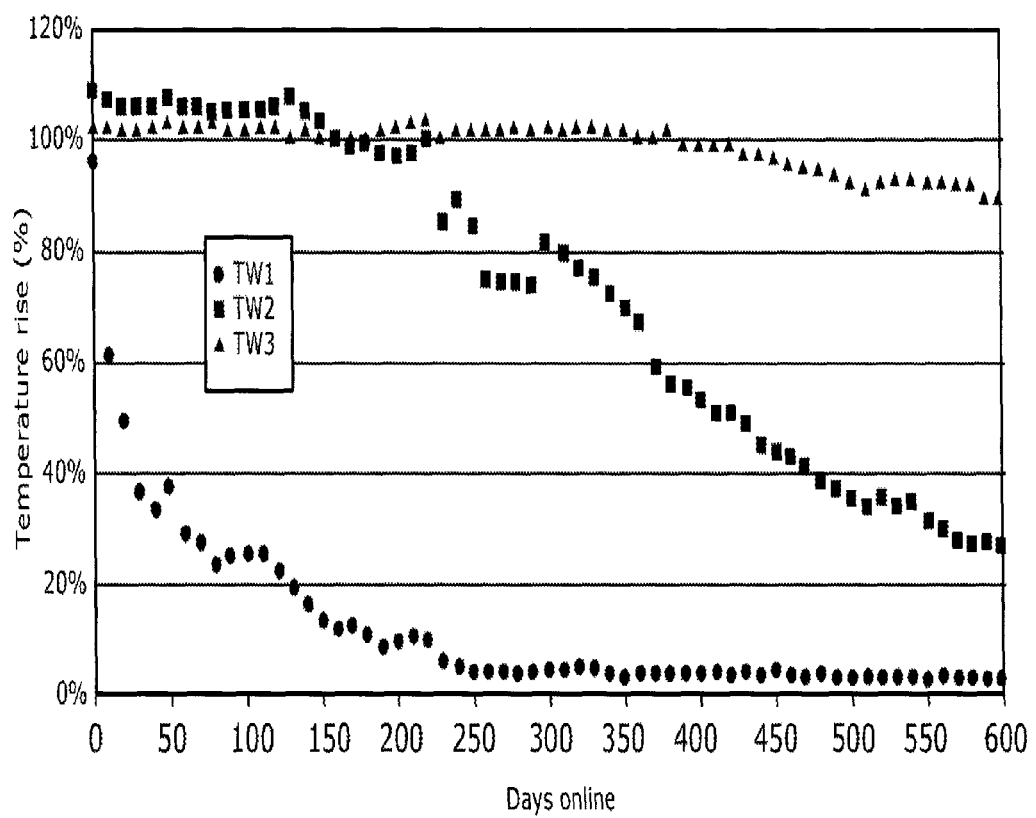

PROCESS FOR ETHYLBENZENE PRODUCTION

CROSS-REFERENCE TO RELATED APPLICATIONS

This application is a Continuation of U.S. application Ser. No. 12/568,007, filed on Sep. 28, 2009, which claims benefit of the Provisional Application No. 61/101,610, filed on Sep. 30, 2008.

FIELD

Embodiments of the present invention generally relate to alkylation of aromatic compounds.

BACKGROUND

Alkylation reactions generally involve contacting a first aromatic compound with an alkylation agent in the presence of a catalyst to form a second aromatic compound. One important alkylation reaction is the reaction of benzene with ethylene in the production of ethylbenzene. The ethylbenzene can then be dehydrogenated to form styrene.

Catalyst life is an important consideration in alkylation reactions. There are the costs related to the catalyst itself, such as the unit cost of the catalyst, the useful life of the catalyst, the ability to regenerate used catalyst, and the cost of disposing of used catalyst. There are also the costs related to shutting down an alkylation reactor to replace the catalyst and/or to regenerate the catalyst bed, which includes labor, materials, and loss of productivity.

Catalyst deactivation can tend to reduce the level of conversion, the level of selectivity, or both, each which can result in an undesirable loss of process efficiency. There can be various reasons for deactivation of alkylation catalysts. These can include the plugging of catalyst surfaces, such as by coke or tars, which can be referred to as carbonization; the physical breakdown of the catalyst structure; and the loss of promoters or additives from the catalyst. Depending upon the catalyst and the various operating parameters that are used, one or more of these mechanisms may apply.

Another cause of catalyst deactivation can be the result of poisons present in an input stream to the alkylation system, for example amine or ammonia compounds. The poisons can react with components of the catalyst leading to deactivation of the component or a restriction in accessing the component within the catalyst structure. The poisons can further act to reduce yields and increase costs. Therefore, a need exists to develop an alkylation system that is capable of reducing alkylation catalyst deactivation or a method of managing alkylation catalyst deactivation in an effective manner.

In view of the above, it would be desirable to have an effective method to produce ethylbenzene in commercial quantities via a catalytic alkylation reaction. It would further be desirable if the method was robust and did not experience frequent disruptions due to process interruptions for catalyst regeneration or replacement.

SUMMARY

Embodiments of the present invention include a method of producing commercial quantities of ethylbenzene by the catalytic alkylation reaction of benzene and ethylene.

Embodiments of the present invention include a method of producing alkylaromatics by the alkylation of an aromatic and an alkylating agent, the method involving providing at least one reaction zone containing H-beta zeolite catalyst into which a feed stream comprising an aromatic and an alkylating agent is introduced. At least a portion of the aromatic is reacted under alkylation conditions to produce an alkylaromatic. A first product stream containing alkylaromatic can then be removed. The aromatic can be benzene, the alkylating agent can be ethylene, and the alkylaromatic can be ethylbenzene. The alkylaromatic production can be least 0.5 million pounds per day and can be between at least 0.5 million pounds per day and 10 million pounds per day.

The at least one reaction zone can include at least one preliminary alkylation reactor and at least one primary alkylation reactor. The at least one preliminary alkylation reactor can contain H-beta zeolite catalyst in a quantity of between at least 5,000 pounds to 50,000 pounds. One or more of the at least one preliminary alkylation reactor and at least one primary alkylation reactor can contain a mixed catalyst that includes the H-beta zeolite catalyst in addition to at least one other catalyst. In an embodiment the primary alkylation reactor experiences a reduced rate of catalyst deactivation when the preliminary alkylation reactor containing H-beta zeolite catalyst is in service. In an embodiment the primary alkylation reactor experiences no catalyst deactivation when the preliminary alkylation reactor containing H-beta zeolite catalyst is in service.

The amount of H-beta catalyst can be between at least 5,000 pounds to 50,000 pounds and can be in a preliminary alkylation system, which can have a run time of at least 6 months, or at least 9 months, or at least 12 months, or at least 18 months prior to regeneration. The H-beta zeolite catalyst in the preliminary alkylation system can be regenerated in-situ. The preliminary alkylation system can be bypassed for catalyst regeneration without taking the at least one primary alkylation reactor out of service.

BRIEF DESCRIPTION OF DRAWINGS

FIG. 5 is a graph of the percent temperature rise data obtained in an Example of the present invention.

DETAILED DESCRIPTION

Figure 1:
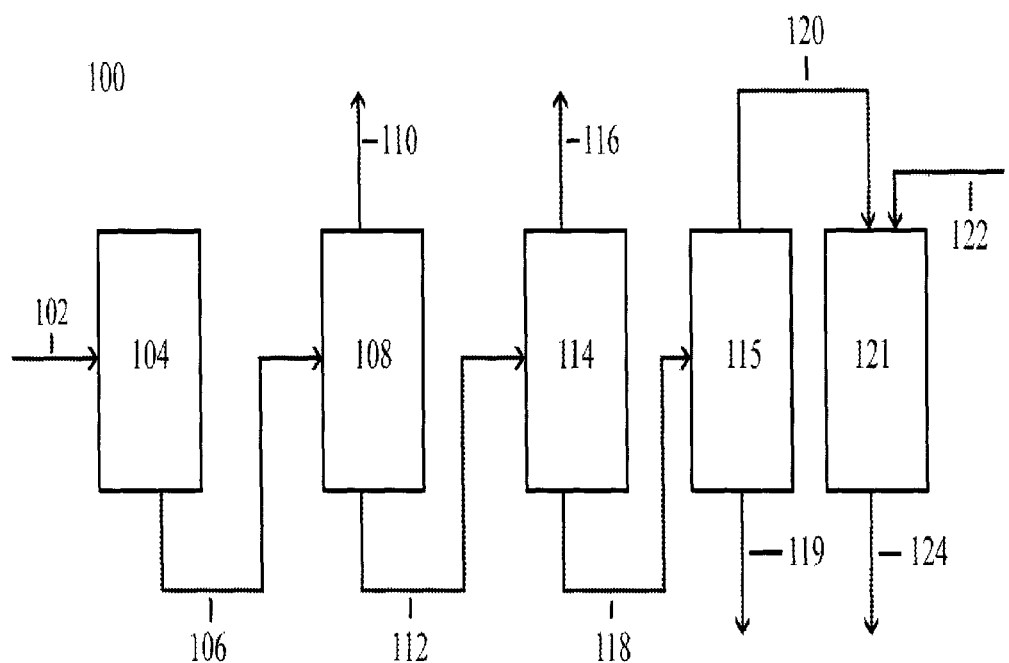
FIG. 1 is a schematic block diagram of an embodiment of an alkylation/transalkylation process.

Aromatic conversion processes carried out over molecular sieve catalysts are well known in the chemical industry. Alkylation reactions of aromatics, such as benzene, to produce a variety of alkyl-benzene derivatives, such as ethylbenzene, are quite common.

Embodiments of the present invention generally relate an alkylation system adapted to minimize process upsets due to alkylation catalyst deactivation and the resulting catalyst regeneration or replacement. In one embodiment of the invention, commercial quantities of H-beta catalyst are used within an alkylation process to produce commercial quantities of ethylbenzene from benzene and ethylene. The process can include one or more fixed catalyst beds of H-beta that can be regenerated either in-situ or ex-situ without significant disruptions to the commercial alkylation production rates.

As used herein commercial quantities of an H-beta alkylation catalyst means a quantity of from 3,000 pounds to 50,000 pounds or more of catalyst in use as an alkylation system within an alkylation process, such as for ethylbenzene production. The H-beta alkylation catalyst can be used as a preliminary alkylation system within an alkylation process for ethylbenzene production. The preliminary alkylation system can be an initial bed or beds in a multi-bed reactor, or can be an initial reactor or group of reactors in a multi-reactor alkylation process, for example. In embodiments of the invention where an H-beta alkylation catalyst is utilized for both the preliminary alkylation system and the primary alkylation system, the catalyst quantity for the total process may range up to 100,000 pounds or more. As used herein commercial quantities of ethylbenzene from the alkylation process can range from an average daily production of 0.5 million pounds up to 10.0 million pounds of ethylbenzene or more.

Zeolite beta catalysts are suitable for use in the present invention and are well known in the art. Zeolite beta catalysts typically have a silica/alumina molar ratio (expressed as $SiO_2/Al_2O_3$) of from about 10 to about 300, or about 15 to about 75, for example. In one embodiment, the zeolite beta may have a low sodium content, e.g., less than about 0.2 wt % expressed as $Na_2O$, or less than about 0.06 wt %, for example. The sodium content may be reduced by any method known to one skilled in the art, such as through ion exchange, for example. Zeolite beta catalysts are characterized by having a high surface area of at least 400 $m^2/g$ based upon the crystalline form without any regard to supplemental components such as binders. In one embodiment, the zeolite beta may have a surface area of at least 600 $m^2/g$. The formation of zeolite beta catalysts is further described in U.S. Pat. No. 3,308,069 to Wadlinger et al and U.S. Pat. No. 4,642,226 to Calvert et al, which are incorporated by reference herein.

An H-beta type zeolite catalyst has the characteristic of having hydrogen as its nominal cation form. Within one particular embodiment a commercially available H-beta catalyst from Zeolyst International with a commercial designation of Zeolyst CP 787 Zeolite H-Beta Extrudate is used in commercial quantities for the production of ethylbenzene by the alkylation reaction of benzene and ethylene.

FIG. 1 illustrates a schematic block diagram of an embodiment of an alkylation/transalkylation process 100. The process 100 generally includes supplying an input stream 102 (e.g., a first input stream) to an alkylation system 104 (e.g., a first alkylation system.) The alkylation system 104 is generally adapted to contact the input stream 102 with an alkylation catalyst to form an alkylation output stream 106 (e.g., a first output stream).

At least a portion of the alkylation output stream 106 passes to a first separation system 108. An overhead fraction is generally recovered from the first separation system 108 via line 110 while at least a portion of the bottoms fraction is passed via line 112 to a second separation system 114.

An overhead fraction is generally recovered from the second separation system 114 via line 116 while at least a portion of a bottoms fraction is passed via line 118 to a third separation system 115. A bottoms fraction is generally recovered from the third separation system 115 via line 119 while at least a portion of an overhead fraction is passed via line 120 to a transalkylation system 121. In addition to the overhead fraction 120, an additional input, such as additional aromatic compound, is generally supplied to the transalkylation system 121 via line 122 and contacts the transalkylation catalyst, forming a transalkylation output 124.

Although not shown herein, the process stream flow may be modified based on unit optimization. For example, at least a portion of any overhead fraction may be recycled as input to any other system within the process. Also, additional process equipment, such as heat exchangers, may be employed throughout the processes described herein and placement of the process equipment can be as is generally known to one skilled in the art. Further, while described in terms of primary components, the streams indicated may include any additional components as known to one skilled in the art.

Figure 4:
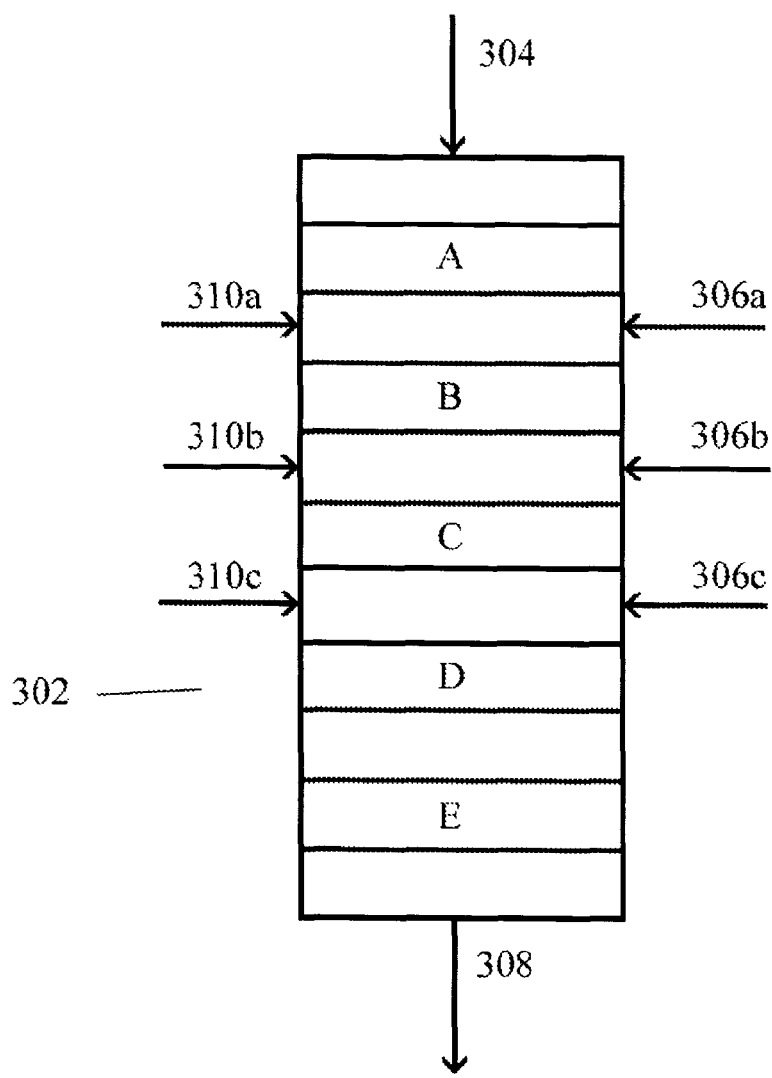
FIG. 4 illustrates one embodiment of an alkylation reactor with a plurality of catalyst beds.

The input stream 102 generally includes an aromatic compound and an alkylating agent. The aromatic compound may include substituted or unsubstituted aromatic compounds. The aromatic compound may include hydrocarbons, such as benzene, for example. If present, the substituents on the aromatic compounds may be independently selected from alkyl, aryl, alkaryl, alkoxy, aryloxy, cycloalkyl, halide and/or other groups that do not interfere with the alkylation reaction, for example. The input stream and alkylating agent 102 can be input at multiple locations as shown in FIG. 4.

The alkylating agent may include olefins such as ethylene or propylene, for example. In one embodiment, the aromatic compound is benzene and the alkylating agent is ethylene, which react to form a product that includes ethylbenzene as a significant component, for example.

In addition to the aromatic compound and the alkylating agent, the input stream 102 may further include other compounds in minor amounts (e.g., sometimes referred to as poisons or inactive compounds). Poisons can be nitrogen components such as ammonia, amine compounds, or nitrites, for example. These poisons can be in quantities in the parts-per-billion (ppb) range, but can have significant effect on the catalyst performance and reduce its useful life. In one embodiment, the input stream 102 includes up to 100 ppb or more of poisons. In one embodiment, the input stream 102 includes poisons typically ranging from 10 ppb to 50 ppb. In one embodiment, the poison content typically averages from 20 ppb to 40 ppb.

Inactive compounds, which can be referred to as inert compounds, such as $C_6$ to $C_8$ aliphatic compounds may also be present. In one embodiment, the input stream 102 includes less than about 5% of such compounds or less than about 1%, for example.

The alkylation system 104 can include a plurality of multi-stage reaction vessels. In one embodiment, the multi-stage reaction vessels can include a plurality of operably connected catalyst beds, such beds containing an alkylation catalyst, such as shown in FIG. 4 for example. Such reaction vessels are generally liquid phase reactors operated at reactor temperatures and pressures sufficient to maintain the alkylation reaction in the liquid phase, i.e., the aromatic compound is in the liquid phase. Such temperatures and pressures are generally determined by individual process parameters. For example, the reaction vessel temperature may be from 65° C. to 300° C., or from 200° C. to 280° C., for example. The reaction vessel pressure may be any suitable pressure in which the alkylation reaction can take place in the liquid phase, such as from 300 psig to 1,200 psig, for example.

In one embodiment, the space velocity of the reaction vessel within the alkylation system 104 is from 10 liquid hourly space velocity (LHSV) per bed to 200 LHSV per bed, based on the aromatic feed rate. In alternate embodiments, the LHSV can range from 10 to 100, or from 10 to 50, or from 10 to 25 per bed. For the alkylation process overall, including all of the alkylation beds of the preliminary alkylation reactor or reactors and the primary alkylation reactor or reactors, the space velocity can range from 1 LHSV to 20 LHSV.

The alkylation output 106 generally includes a second aromatic compound. In one embodiment, the second aromatic compound includes ethylbenzene, for example.

A first separation system 108 may include any process or combination of processes known to one skilled in the art for the separation of aromatic compounds. For example, the first separation system 108 may include one or more distillation columns (not shown,) either in series or in parallel. The number of such columns may depend on the volume of the alkylation output 106 passing through.

The overhead fraction 110 from the first separation system 108 generally includes the first aromatic compound, such as benzene, for example.

The bottoms fraction 112 from the first separation system 108 generally includes the second aromatic compound, such as ethylbenzene, for example.

A second separation system 114 may include any process known to one skilled in the art, for example, one or more distillation columns (not shown), either in series or in parallel.

The overhead fraction 116 from the second separation system 114 generally includes the second aromatic compound, such as ethylbenzene, which may be recovered and used for any suitable purpose, such as the production of styrene, for example.

The bottoms fraction 118 from the second separation system 114 generally includes heavier aromatic compounds, such as polyethylbenzene, cumene and/or butylbenzene, for example.

A third separation system 115 generally includes any process known to one skilled in the art, for example, one or more distillation columns (not shown), either in series or in parallel.

In a specific embodiment, the overhead fraction 120 from the third separation system 115 may include diethylbenzene and triethylbenzene, for example. The bottoms fraction 119 (e.g., heavies) may be recovered from the third separation system 115 for further processing and recovery (not shown).

The transalkylation system 121 generally includes one or more reaction vessels having a transalkylation catalyst disposed therein. The reaction vessels may include any reaction vessel, combination of reaction vessels and/or number of reaction vessels (either in parallel or in series) known to one skilled in the art.

A transalkylation output 124 generally includes the second aromatic compound, for example, ethylbenzene. The transalkylation output 124 can be sent to one of the separation systems, such as the second separation system 114, for separation of the components of the transalkylation output 124.

In one embodiment, the transalkylation system 121 is operated under liquid phase conditions. For example, the transalkylation system 121 may be operated at a temperature of from about 65° C. to about 290° C. and a pressure of about 800 psig or less.

In a specific embodiment, the input stream 102 includes benzene and ethylene. The benzene may be supplied from a variety of sources, such as for example; a fresh benzene source and/or a variety of recycle sources. As used herein, the term "fresh benzene source" refers to a source including at least about 95 wt % benzene, at least about 98 wt % benzene or at least about 99 wt % benzene, for example. In one embodiment, the molar ratio of benzene to ethylene may be from about 1:1 to about 30:1, or from about 1:1 to about 20:1, for the total alkylation process including all of the alkylation beds, for example. The molar ratio of benzene to ethylene for individual alkylation beds can range from 10:1 to 100:1, for example.

In a specific embodiment, benzene is recovered through line 110 and recycled (not shown) as input to the alkylation system 104, while ethylbenzene and/or polyalkylated benzenes are recovered via line 112.

As previously discussed, the alkylation system 104 generally includes an alkylation catalyst. The input stream 102, e.g., benzene/ethylene, contacts the alkylation catalyst during the alkylation reaction to form the alkylation output 106, e.g., ethylbenzene.

Unfortunately, alkylation catalyst systems generally experience deactivation requiring either regeneration or replacement. Additionally, alkylation processes generally require periodic maintenance. Both circumstances generally produce disruptions for liquid phase alkylation processes. The deactivation results from a number of factors. One of those factors is that poisons present in the input stream 102, such as nitrogen, sulfur and/or oxygen containing impurities, either naturally occurring or a result of a prior process, may reduce the activity of the alkylation catalyst.

Embodiments of the invention provide a process wherein continuous production during catalyst regeneration and maintenance may be achieved. For example, one reactor may be taken off-line for regeneration of the catalyst, either by in-situ or ex-situ methods, while the remaining reactor may remain on-line for production. The determination of when such regeneration will be required can depend on specific system conditions, but is generally a predetermined set point (e.g., catalyst productivity, temperature, or time).

If in-situ regeneration is not possible, when removing the catalyst from the reactor for regeneration, it may be possible to replace the catalyst and place the reactor on-line while the removed/deactivated catalyst is regenerated. In such an embodiment, the cost of replacing the catalyst can be large and therefore it is beneficial that such catalyst should have a long life before regeneration. Embodiments of the invention may provide an alkylation system capable of extended catalyst life and extended production runs.

Figure 2:
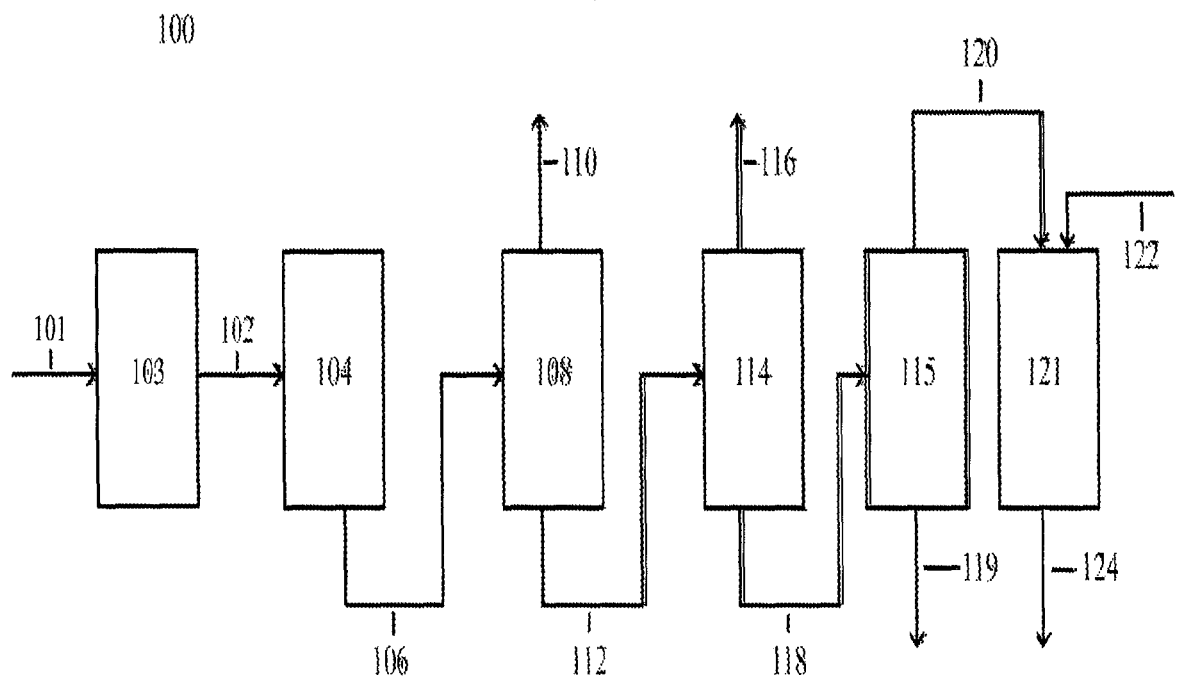
FIG. 2 is a schematic block diagram of an embodiment of an alkylation/transalkylation process that includes a preliminary alkylation step.

Referring to FIG. 2, the alkylation/transalkylation system 100 may further include a preliminary alkylation system 103. The preliminary alkylation system 103 may be maintained at alkylation conditions, for example. The preliminary alkylation input stream 101 may be passed through the preliminary alkylation system 103 prior to entry into the alkylation system 104 to reduce the level of poisons in the input stream 102, for example. In one embodiment, the level of poisons is reduced by at least 10%, or at least 25% or at least 40% or at least 60% or at least 80%, for example. For example, the preliminary alkylation system 103 may be used as a sacrificial system, thereby reducing the amount of poisons contacting the alkylation catalyst in the alkylation system 104 and reducing the frequency of regeneration needed of the alkylation catalyst in the alkylation system 104.

In one embodiment the preliminary alkylation input stream 101 comprises the entire benzene feed to the process and a portion of the ethylene feed to the process. This feed passes through the preliminary alkylation system 103 that contains the zeolite beta catalyst prior to entry into the alkylation system 104 to reduce the level of poisons contacting the alkylation catalyst in the alkylation system 104. The output stream 102 from the preliminary alkylation system 103 can include unreacted benzene and ethylbenzene produced from the preliminary alkylation system 103. Additional ethylene can be added to the alkylation system 104 (not shown in FIG. 2) to react with the unreacted benzene. In this embodiment the preliminary alkylation system 103 can reduce the level of poisons in the benzene and that portion of the ethylene feed that is added to the process preliminary alkylation input stream 101. Ethylene that is added after the preliminary alkylation system 103, such as to the alkylation system 104, would not have a reduction in the level of poisons from the preliminary alkylation system 103.

The preliminary alkylation system 103 may be operated under liquid phase conditions. For example, the preliminary alkylation system 103 may be operated at a temperature of from about 100° C. to about 300° C., or from 200° C. to about 280° C., and a pressure to ensure liquid phase conditions, such as from about 300 psig to about 1200 psig.

The preliminary alkylation system 103 generally includes a preliminary catalyst (not shown) disposed therein. The alkylation catalyst, transalkylation catalyst and/or the preliminary catalyst may be the same or different. In general, such catalysts are selected from molecular sieve catalysts, such as zeolite beta catalysts, for example.

As a result of the level of poisons present in the preliminary alkylation input 101, the preliminary catalyst in the preliminary alkylation system 103 may become deactivated, requiring regeneration and/or replacement. For example, the preliminary catalyst may experience deactivation more rapidly than the alkylation catalyst.

Embodiments of the invention can utilize a H-beta zeolite catalyst in the preliminary alkylation system 103. In addition the alkylation reaction may also utilize such H-beta catalyst. Embodiments can include the preliminary alkylation system having a mixed catalyst load that includes a H-beta zeolite catalyst and one or more other catalyst. The mixed catalyst load can, for example, be a layering of the various catalysts, either with or without a barrier or separation between them, or alternately can include a physical mixing where the various catalysts are in contact with each other. Embodiments can include the alkylation system having a mixed catalyst load that includes a H-beta zeolite catalyst and one or more other catalyst. The mixed catalyst load can, for example, be a layering of the various catalysts, either with or without a barrier or separation between them, or alternately can include a physical mixing where the various catalysts are in contact with each other.

When regeneration of any catalyst within the system is desired, the regeneration procedure generally includes processing the deactivated catalyst at high temperatures, although the regeneration may include any regeneration procedure known to one skilled in the art.

Once a reactor is taken off-line, the catalyst disposed therein may be purged. Off-stream reactor purging may be performed by contacting the catalyst in the off-line reactor with a purging stream, which may include any suitable inert gas (e.g., nitrogen), for example. The off-stream reactor purging conditions are generally determined by individual process parameters and are generally known to one skilled in the art.

The catalyst may then undergo regeneration. The regeneration conditions may be any conditions that are effective for at least partially reactivating the catalyst and are generally known to one skilled in the art. For example, regeneration may include heating the alkylation catalyst to a temperature or a series of temperatures, such as a regeneration temperature of from about 200° C. to about 500° C. above the purging or alkylation reaction temperature, for example.

In one embodiment, the alkylation catalyst is heated to a first temperature (e.g., 400° C.) with a gas containing nitrogen and 2 mol % or less oxygen, for example, for a time sufficient to provide an output stream having an oxygen content of about 0.1 mol %. The regeneration conditions will generally be controlled by the alkylation system restrictions and/or operating permit requirements that can regulate conditions, such as the permissible oxygen content that can be sent to flare for emission controls. The alkylation catalyst may then be heated to a second temperature (e.g., 500° C.) for a time sufficient to provide an output stream having a certain oxygen content. The catalyst may further be held at the second temperature for a period of time, or at a third temperature that is greater than the second temperature, for example. Upon catalyst regeneration, the reactor is allowed to cool and can then be made ready to be placed on-line for continued production.

Figure 3:
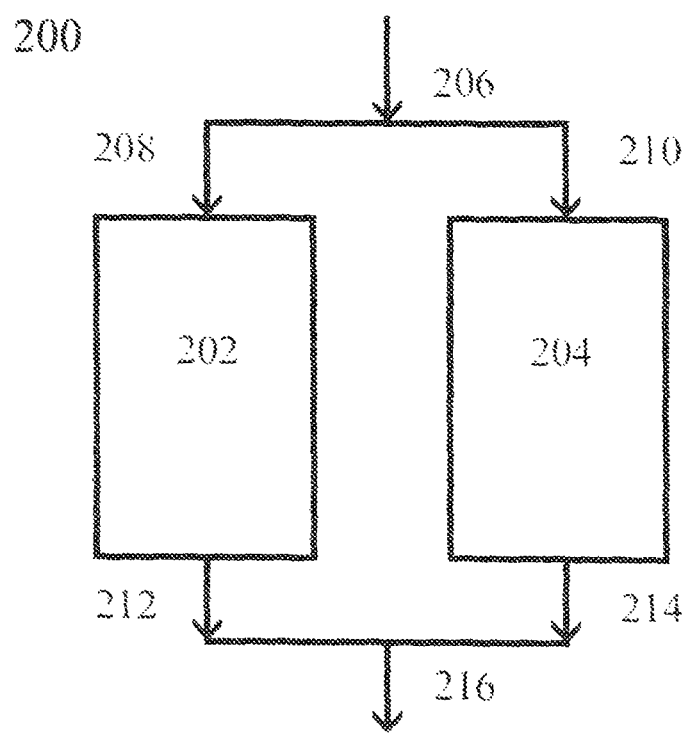
FIG. 3 is a schematic illustration of a parallel reactor system that can be used for a preliminary alkylation step.

FIG. 3 illustrates a non-limiting embodiment of an alkylation system 200, which can be a preliminary alkylation system. The alkylation system 200 shown includes a plurality of alkylation reactors, such as two alkylation reactors 202 and 204, operating in parallel. One or both alkylation reactors 202 and 204, which may be the same type of reaction vessel, or, in certain embodiments, may be different types of reaction vessels, may be placed in service at the same time. For example, only one alkylation reactor may be on line while the other is undergoing maintenance, such as catalyst regeneration. In one embodiment, the alkylation system 200 is configured so that the input stream is split to supply approximately the same input to each alkylation reactor 202 and 204. However, such flow rates will be determined by each individual system.

This mode of operation (e.g., multiple parallel reactors) may involve operation of the individual reactors at relatively lower space velocities for prolonged periods of time with periodic relatively short periods of operation at enhanced, relatively higher space velocities when one reactor is taken off-stream. By way of example, during normal operation of the system 200, with both reactors 202 and 204 on-line, the input 206 stream may be supplied to each reactor (e.g., via lines 208 and 210) to provide a reduced space velocity. The output 216 stream may be the combined flow from each reactor (e.g., via lines 212 and 214). When a reactor is taken off-line and the feed rate continues unabated, the space velocity for the remaining reactor may approximately double.

In a specific embodiment, one or more of the plurality of alkylation reactors may include a plurality of interconnected catalyst beds. The plurality of catalyst beds may include from 2 to 15 beds, or from 5 to 10 beds or, in specific embodiments, 5 or 8 beds, for example. Embodiments can include one or more catalyst beds having a mixed catalyst load that includes a H-beta zeolite catalyst and one or more other catalyst. The mixed catalyst load can, for example, be a layering of the various catalysts, either with or without a barrier or separation between them, or alternately can include a physical mixing where the various catalysts are in contact with each other.

FIG. 4 illustrates a non-limiting embodiment of an alkylation reactor 302. The alkylation reactor 302 includes five series connected catalyst beds designated as beds A, B, C, D, and E. An input stream 304 (e.g., benzene/ethylene) is introduced to the reactor 302, passing through each of the catalyst beds to contact the alkylation catalyst and form the alkylation output 308. Additional alkylating agent may be supplied via lines 306a, 306b, and 306c to the interstage locations in the reactor 302. Additional aromatic compound may also be introduced to the interstage locations via lines 310a, 310b and 310c, for example.

EXAMPLE

In Example 1 a process of making ethylbenzene using commercial quantities of a H-beta zeolite includes a preliminary alkylation system having a single reactor loaded with approximately 22,000 pounds of H-beta zeolite catalyst. The process further comprises a primary alkylation system after the preliminary alkylation system that contains catalyst other than the H-beta zeolite catalyst.

The feed stream to the process can contain impurities such as acetonitrile, ammonia, and/or amine compounds, for example, in quantities that range from 1 ppb to 100 ppb or more and can typically average from 20 ppb to 40 ppb. The preliminary alkylation system can remove impurities in the benzene feed and a portion of the ethylene feed to the process prior to the primary alkylation system. The H-beta catalyst is commercially available from Zeolyst International with a commercial designation of Zeolyst CP 787 Zeolite H-Beta Extrudate.

The benzene feed is added to the preliminary alkylation reactor at a rate of approximately 700,000 to 750,000 pounds per hour, passes through the preliminary alkylation reactor and then to the primary alkylation system. The benzene feed is equivalent to approximately 15 to 20 LHSV for the preliminary alkylation reactor.

Ethylene is added to both the preliminary alkylation reactor and to the primary alkylation system. Ethylene is added to the process in a benzene:ethylene molar ratio typically ranging from between 15:1 to 20:1 for the preliminary alkylation reactor and for each catalyst bed within the primary alkylation system. The process, including the preliminary alkylation reactor and the primary alkylation system, has an overall benzene:ethylene molar ratio typically ranging from between 2.7:1 to 3.7:1. Conversion of benzene to ethylbenzene in the preliminary alkylation reactor results in about 1.0 million pounds per day of the total ethylbenzene production. The process, including the preliminary alkylation reactor and the primary alkylation system, has an overall production rate of about 7.5 million pounds of ethylbenzene per day.

During Example 1 the primary alkylation reaction beds did not shown significant signs of deactivation, indicating that the preliminary bed is containing, reacting or deactivating the poisons that are present in the benzene feed.

Table 1 provides selected data obtained from Example 1. The data is presented as a percentage of the overall temperature rise in the preliminary alkylation reactor that has occurred at specific locations. Thermocouple #1 (TW #1) provides the temperature reading at a point approximately 11% into the length of the preliminary alkylation reactor catalyst bed and thereby can give an indication of the amount of reaction that has occurred in the first 11% of the bed, which represents about 2,400 pounds of catalyst. Thermocouple #2 (TW #2) is approximately 31% through the preliminary alkylation reactor catalyst bed, which represents about 6,800 pounds of catalyst, while thermocouple #3 (TW #3) is approximately 47% through the preliminary alkylation reactor catalyst bed, which represents about 10,300 pounds of catalyst, and thermocouple #4 (TW #4) is approximately 64% through the preliminary alkylation reactor catalyst bed, which represents about 14,100 pounds of catalyst. The data in Table 1 is not normalized to force a maximum percent rise to 100%. Values of over 100% can be due to temperature reading variations among the various instruments.

The temperature profiles of the preliminary alkylation reactor catalyst bed indicate where the catalytic reaction is occurring and the extent of catalyst deactivation along the length of the bed. As the catalyst deactivates and the active reaction zone proceeds down the length of the bed to catalyst that is active, the temperature rise profile can be observed to progress down the reactor. For example if the percent rise at TW #1 is 50%, then approximately 50% of the entire temperature rise throughout the preliminary catalyst bed is occurring within the first 11% of the bed. If later the percent rise at TW #1 value decreases to 20%, that would indicate that the catalyst in the first 11% of the catalyst bed has deactivated to an extent that only 20% of the temperature rise is occurring in the first 11% of the bed length while 80% of the rise is occurring after the first 11% of the catalyst bed length.

The preliminary alkylation reactor containing H-beta zeolite catalyst was in service for over 580 days without requiring regeneration. FIG. 5 illustrates the temperature trend data for TW #1, TW #2 and TW #3 for the first 600 days of Example 1. The data points shown are the percent rise on approximately every 10 days. FIG. 5 is only to illustrate the trends in the data of Table 1 and should not be taken to supersede Table 1 in any way. Upon 100 days service, the percent rise at TW #1 (11% into the length of the reactor) had decreased from an initial 89% to around 25%, while the percent rise at TW #2 (31% into the length of the reactor) had not shown any appreciable decrease. Upon 200 days service, the percent rise at TW #1 had decreased to around 10%, while the percent rise at TW #2 had decreased to around 95%, while the percent rise at TW #3 (47% into the length of the reactor) had not shown any appreciable decrease. Upon 300 days service, the percent rise at TW #1 had decreased to around 5%, the percent rise at TW #2 had decreased to around 80%, while the percent rise at TW #3 had not shown any appreciable decrease. Upon 400 days service, the percent rise at TW #1 had decreased to less than 5%, the percent rise at TW #2 had decreased to around 55%, while the percent rise at TW #3 had just started to indicate a decrease. Upon 500 days service, the percent rise at TW #1 had decreased to around 2%, the percent rise at TW #2 had decreased to around 35%, the percent rise at TW #3 had decreased to around 94%, while the percent rise at TW #4 (64% into the length of the reactor) had not shown any appreciable decrease. Upon 600 days service, the percent rise at TW #1 was still around 2%, the percent rise at TW #2 had decreased to around 26%, the percent rise at TW #3 had decreased to around 90%, while the percent rise at TW #4 (64% into the length of the reactor) had still not shown any appreciable decrease. During Example 1 the rate of deactivation of the catalyst in the primary alkylation reactor located after the preliminary alkylation reactor was less than the rate of deactivation prior to having the preliminary alkylation reactor in service. There was a reduction of catalyst deactivation in the primary alkylation system, indicating the preliminary alkylation reactor was able to contain or react with poisons contained in the benzene feed such that they had a reduced effect on the catalyst in the primary alkylation system.

A total of about 1,360 million pounds of EB was produced by the process during the first 190 days of Example 1, of which 181 days had online production, with a deactivation of about ninety percent of the catalyst load in the preliminary alkylation reactor up to TW #1 and twenty percent of the catalyst load between TW#1 to TW #2, which equates to about 3,000 pounds of deactivated catalyst. This portion of Example 1 provided about 0.45 million pounds of EB production per pound of catalyst deactivation in the preliminary alkylation reactor, or alternatively had a deactivation of about 2.2 pounds of catalyst per million pounds of EB produced.

A total of about 2,625 million pounds of EB was produced by the process during the first 365 days of Example 1, of which 350 days had online production, with a deactivation of about 96% of the catalyst load in the preliminary alkylation reactor up to TW #1 and 30% of the catalyst load between TW#1 to TW #2, which equates to about 3,600 pounds of deactivated catalyst. The first 350 days of online production provided a deactivation of about 1.4 pounds of catalyst per million pounds of EB produced.

A total of about 4,350 million pounds of EB was produced by the process during the first 595 days of Example 1, of which 580 days had online production, with a deactivation of about 97% of the catalyst load in the preliminary alkylation reactor up to TW #1, 79% of the catalyst load between TW #1 to TW #2, and 15% of the catalyst load between TW #2 to TW #3, which equates to about 6,330 pounds of deactivated catalyst. The first 580 days of online production of Example 1 provided a deactivation of about 1.45 pounds of catalyst per million pounds of EB produced.

Referring to FIG. 5, although the catalyst contained in the first 11% of the preliminary alkylation reactor bed had been in service for 580 days, it was still providing about 3% of the temperature rise across the preliminary alkylation reactor, indicating that it still had some activity. The decline curve for TW #2 is less steep than that of TW #1, indicating that the catalyst before the TW #1 location in the catalyst bed is reducing the effect of poisons present in the benzene feed on the catalyst down stream, thus extending its useful catalyst life. The decline in the TW #3 curve is less steep than that of TW #1 during its initial deactivation and is less steep than that of TW #2, further indicating that the catalyst before the TW #2 location in the catalyst bed is removing a significant amount of the poisons present in the feed, thus extending the useful catalyst life of the catalyst down stream.

An embodiment of the present invention involves a process of producing ethylbenzene from a high poison feed stream by the alkylation of benzene with ethylene utilizing an H-beta zeolite catalyst that has a catalyst deactivation rate that is no more than 30 pounds of catalyst per million pounds of EB produced. Additional embodiments include a process having a catalyst deactivation rate that is no more than 20 pounds of catalyst per million pounds of EB produced, no more than 10 pounds of catalyst per million pounds of EB produced, no more than 7.5 pounds of catalyst per million pounds of EB produced, no more than 5 pounds of catalyst per million pounds of EB produced, no more than 2.5 pounds of catalyst per million pounds of EB produced, no more than 2.0 pounds of catalyst per million pounds of EB produced, and no more than 1.5 pounds of catalyst per million pounds of EB produced.

TABLE 1

Preliminary Alkylation Reactor Data

| Date | Overall temp rise ° F. | TW #1 temp rise | TW #2 temp rise | TW #3 temp rise | TW #4 temp rise |
|---|---|---|---|---|---|
| Jan. 22, 2008 | 47.5 | 89% | 109% | 102% | 102% |
| Jan. 23, 2008 | 53.0 | 87% | 108% | 102% | 103% |
| Jan. 24, 2008 | 53.5 | 84% | 107% | 103% | 103% |
| Jan. 25, 2008 | 54.5 | 75% | 106% | 103% | 103% |
| Jan. 26, 2008 | 53.7 | 72% | 108% | 103% | 103% |
| Jan. 27, 2008 | 53.7 | 71% | 108% | 102% | 103% |
| Jan. 28, 2008 | 54.1 | 70% | 107% | 102% | 102% |
| Jan. 29, 2008 | 54.5 | 64% | 108% | 102% | 103% |
| Jan. 30, 2008 | 54.9 | 63% | 108% | 103% | 104% |
| Jan. 31, 2008 | 54.8 | 63% | 107% | 102% | 103% |
| Feb. 01, 2008 | 55.0 | 59% | 107% | 102% | 103% |
| Feb. 02, 2008 | 55.5 | 58% | 106% | 101% | 102% |
| Feb. 03, 2008 | 55.4 | 56% | 106% | 101% | 101% |
| Feb. 04, 2008 | 55.7 | 55% | 106% | 101% | 101% |
| Feb. 05, 2008 | 56.0 | 54% | 106% | 101% | 102% |
| Feb. 06, 2008 | 55.4 | 55% | 107% | 102% | 103% |
| Feb. 07, 2008 | 55.9 | 54% | 107% | 102% | 103% |
| Feb. 08, 2008 | 56.3 | 53% | 107% | 102% | 102% |
| Feb. 09, 2008 | 56.8 | 52% | 106% | 102% | 102% |
| Feb. 10, 2008 | 56.8 | 51% | 106% | 101% | 102% |
| Feb. 11, 2008 | 56.5 | 50% | 106% | 101% | 102% |
| Feb. 12, 2008 | 56.4 | 48% | 107% | 102% | 103% |
| Feb. 13, 2008 | 56.7 | 45% | 107% | 103% | 104% |
| Feb. 14, 2008 | 56.5 | 44% | 107% | 102% | 102% |
| Feb. 15, 2008 | 56.7 | 43% | 106% | 102% | 102% |
| Feb. 16, 2008 | 56.9 | 42% | 106% | 102% | 102% |
| Feb. 17, 2008 | 56.7 | 41% | 106% | 102% | 102% |
| Feb. 18, 2008 | 55.3 | 40% | 107% | 102% | 103% |
| Feb. 19, 2008 | 53.5 | 38% | 106% | 102% | 102% |
| Feb. 20, 2008 | 52.2 | 36% | 106% | 101% | 102% |
| Feb. 21, 2008 | 55.4 | 37% | 105% | 101% | 102% |
| Feb. 22, 2008 | 56.1 | 37% | 106% | 102% | 103% |
| Feb. 23, 2008 | 56.2 | 37% | 106% | 102% | 102% |
| Feb. 24, 2008 | 56.1 | 36% | 106% | 102% | 102% |
| Feb. 25, 2008 | 56.2 | 35% | 105% | 101% | 102% |
| Feb. 26, 2008 | 56.3 | 35% | 107% | 103% | 103% |
| Feb. 27, 2008 | 55.4 | 35% | 107% | 103% | 104% |
| Feb. 28, 2008 | 55.4 | 34% | 106% | 102% | 102% |
| Feb. 29, 2008 | 55.5 | 33% | 106% | 101% | 102% |
| Mar. 01, 2008 | 55.4 | 33% | 106% | 102% | 102% |
| Mar. 02, 2008 | 55.6 | 32% | 105% | 101% | 102% |
| Mar. 03, 2008 | 55.5 | 32% | 106% | 102% | 103% |
| Mar. 04, 2008 | 55.6 | 32% | 106% | 103% | 104% |
| Mar. 05, 2008 | 55.3 | 31% | 106% | 102% | 103% |
| Mar. 06, 2008 | 55.5 | 31% | 106% | 102% | 103% |
| Mar. 07, 2008 | 55.6 | 30% | 107% | 103% | 105% |
| Mar. 08, 2008 | 55.2 | 31% | 106% | 103% | 103% |
| Mar. 09, 2008 | 55.3 | 30% | 106% | 102% | 103% |
| Mar. 10, 2008 | 53.8 | 34% | 107% | 102% | 103% |
| Mar. 11, 2008 | 52.5 | 37% | 108% | 103% | 104% |
| Mar. 12, 2008 | 52.7 | 38% | 108% | 103% | 103% |
| Mar. 13, 2008 | 53.2 | 30% | 105% | 102% | 102% |
| Mar. 14, 2008 | 53.7 | 26% | 104% | 101% | 101% |
| Mar. 15, 2008 | 53.5 | 27% | 104% | 102% | 102% |
| Mar. 16, 2008 | 53.8 | 26% | 104% | 101% | 102% |
| Mar. 17, 2008 | 54.8 | 25% | 103% | 101% | 101% |
| Mar. 18, 2008 | 55.1 | 24% | 103% | 101% | 101% |
| Mar. 19, 2008 | 55.1 | 24% | 104% | 102% | 103% |
| Mar. 20, 2008 | 55.8 | 25% | 104% | 102% | 103% |
| Mar. 21, 2008 | 55.3 | 25% | 104% | 102% | 102% |
| Mar. 22, 2008 | 54.6 | 28% | 106% | 102% | 103% |
| Mar. 23, 2008 | 54.8 | 33% | 107% | 103% | 104% |
| Mar. 24, 2008 | 56.1 | 25% | 105% | 104% | 104% |
| Mar. 25, 2008 | 56.9 | 24% | 104% | 102% | 102% |
| Mar. 26, 2008 | 55.9 | 24% | 104% | 102% | 102% |
| Mar. 29, 2008 | 55.5 | 23% | 104% | 101% | 102% |
| Mar. 30, 2008 | 55.4 | 23% | 103% | 101% | 102% |
| Mar. 31, 2008 | 57.6 | 23% | 101% | 99% | 101% |
| Apr. 01, 2008 | 53.9 | 22% | 103% | 101% | 102% |
| Apr. 02, 2008 | 49.8 | 26% | 106% | 103% | 104% |
| Apr. 03, 2008 | 41.3 | 26% | 106% | 102% | 103% |
| Apr. 04, 2008 | 55.6 | 25% | 104% | 102% | 102% |
| Apr. 05, 2008 | 54.0 | 23% | 104% | 103% | 103% |
| Apr. 06, 2008 | 55.7 | 23% | 103% | 101% | 102% |
| Apr. 07, 2008 | 56.7 | 24% | 104% | 101% | 102% |
| Apr. 08, 2008 | 20.2 | 30% | 116% | 104% | 107% |
| Apr. 09, 2008 | 57.3 | 23% | 103% | 101% | 102% |
| Apr. 10, 2008 | 57.0 | 22% | 103% | 101% | 101% |
| Apr. 11, 2008 | 53.2 | 22% | 101% | 100% | 100% |
| Apr. 12, 2008 | 44.5 | 27% | 106% | 104% | 104% |
| Apr. 13, 2008 | 54.4 | 22% | 104% | 103% | 104% |
| Apr. 14, 2008 | 56.1 | 21% | 103% | 103% | 104% |
| Apr. 15, 2008 | 56.8 | 21% | 102% | 102% | 103% |
| Apr. 16, 2008 | 56.4 | 21% | 102% | 101% | 102% |
| Apr. 17, 2008 | 55.6 | 23% | 104% | 101% | 102% |
| Apr. 18, 2008 | 54.7 | 25% | 106% | 102% | 103% |
| Apr. 19, 2008 | 54.8 | 25% | 106% | 102% | 103% |
| Apr. 20, 2008 | 54.7 | 25% | 106% | 102% | 102% |
| Apr. 21, 2008 | 54.8 | 24% | 105% | 102% | 102% |
| Apr. 22, 2008 | 54.6 | 23% | 105% | 101% | 102% |
| Apr. 23, 2008 | 64.8 | 24% | 105% | 101% | 101% |
| Apr. 24, 2008 | 55.0 | 22% | 105% | 101% | 101% |
| Apr. 25, 2008 | 10.8 | 42% | 136% | 111% | 112% |
| Apr. 26, 2008 | 54.0 | 25% | 106% | 102% | 103% |
| Apr. 27, 2008 | 55.8 | 23% | 106% | 102% | 103% |
| Apr. 28, 2008 | 54.7 | 22% | 105% | 102% | 103% |
| Apr. 29, 2008 | 54.3 | 21% | 105% | 102% | 103% |
| Apr. 30, 2008 | 54.6 | 22% | 104% | 102% | 102% |
| May 01, 2008 | 54.0 | 24% | 105% | 101% | 101% |

TABLE 1-continued

Preliminary Alkylation Reactor Data

| Date | Overall temp rise ° F. | TW #1 temp rise | TW #2 temp rise | TW #3 temp rise | TW #4 temp rise |
|---|---|---|---|---|---|
| May 02, 2008 | 51.8 | 21% | 103% | 102% | 102% |
| May 03, 2008 | 47.0 | 28% | 109% | 102% | 104% |
| May 04, 2008 | 47.4 | 29% | 108% | 103% | 104% |
| May 05, 2008 | 47.0 | 30% | 109% | 103% | 103% |
| May 06, 2008 | 44.1 | 31% | 109% | 102% | 103% |
| May 07, 2008 | 44.2 | 31% | 109% | 102% | 102% |
| May 08, 2008 | 43.2 | 31% | 109% | 103% | 103% |
| May 15, 2008 | 46.0 | 30% | 109% | 105% | 106% |
| May 16, 2008 | 54.4 | 24% | 106% | 102% | 103% |
| May 17, 2008 | 54.2 | 24% | 106% | 102% | 103% |
| May 18, 2008 | 54.4 | 24% | 106% | 102% | 102% |
| May 19, 2008 | 53.7 | 24% | 105% | 102% | 102% |
| May 20, 2008 | 55.4 | 25% | 106% | 102% | 102% |
| May 21, 2008 | 55.5 | 26% | 106% | 101% | 102% |
| May 22, 2008 | 55.6 | 25% | 106% | 101% | 102% |
| May 23, 2008 | 55.0 | 24% | 106% | 101% | 101% |
| May 24, 2008 | 53.3 | 28% | 107% | 101% | 102% |
| May 25, 2008 | 51.9 | 29% | 107% | 101% | 102% |
| May 26, 2008 | 47.3 | 34% | 109% | 101% | 102% |
| May 27, 2008 | 51.1 | 31% | 108% | 102% | 102% |
| May 28, 2008 | 50.0 | 26% | 107% | 102% | 102% |
| May 29, 2008 | 49.4 | 25% | 106% | 101% | 102% |
| May 30, 2008 | 49.2 | 25% | 106% | 101% | 101% |
| May 31, 2008 | 49.1 | 24% | 106% | 101% | 102% |
| Jun. 01, 2008 | 49.3 | 24% | 106% | 101% | 102% |
| Jun. 02, 2008 | 54.7 | 20% | 103% | 101% | 101% |
| Jun. 03, 2008 | 56.2 | 18% | 103% | 101% | 101% |
| Jun. 04, 2008 | 56.3 | 18% | 102% | 101% | 101% |
| Jun. 05, 2008 | 56.1 | 19% | 103% | 101% | 101% |
| Jun. 06, 2008 | 55.9 | 18% | 103% | 100% | 101% |
| Jun. 07, 2008 | 55.9 | 18% | 103% | 100% | 101% |
| Jun. 08, 2008 | 55.6 | 19% | 103% | 101% | 101% |
| Jun. 09, 2008 | 55.8 | 18% | 103% | 100% | 101% |
| Jun. 10, 2008 | 55.8 | 18% | 103% | 100% | 101% |
| Jun. 11, 2008 | 55.7 | 18% | 103% | 101% | 101% |
| Jun. 12, 2008 | 56.5 | 18% | 102% | 100% | 101% |
| Jun. 13, 2008 | 55.9 | 17% | 102% | 100% | 101% |
| Jun. 14, 2008 | 55.9 | 18% | 103% | 101% | 101% |
| Jun. 15, 2008 | 55.9 | 18% | 103% | 101% | 102% |
| Jun. 16, 2008 | 56.0 | 17% | 102% | 101% | 101% |
| Jun. 17, 2008 | 55.6 | 17% | 102% | 101% | 102% |
| Jun. 18, 2008 | 55.6 | 17% | 102% | 101% | 102% |
| Jun. 19, 2008 | 55.7 | 17% | 102% | 101% | 101% |
| Jun. 20, 2008 | 55.7 | 17% | 102% | 101% | 101% |
| Jun. 21, 2008 | 55.7 | 17% | 102% | 100% | 101% |
| Jun. 22, 2008 | 55.7 | 16% | 102% | 101% | 101% |
| Jun. 23, 2008 | 55.6 | 16% | 102% | 101% | 102% |
| Jun. 24, 2008 | 56.4 | 15% | 100% | 100% | 101% |
| Jun. 25, 2008 | 56.5 | 15% | 99% | 100% | 101% |
| Jun. 26, 2008 | 56.5 | 15% | 100% | 100% | 101% |
| Jun. 27, 2008 | 56.5 | 15% | 99% | 100% | 102% |
| Jun. 28, 2008 | 56.4 | 14% | 99% | 101% | 102% |
| Jun. 29, 2008 | 56.5 | 15% | 99% | 101% | 102% |
| Jun. 30, 2008 | 56.5 | 14% | 98% | 100% | 102% |
| Jul. 01, 2008 | 49.0 | 20% | 106% | 102% | 103% |
| Jul. 02, 2008 | 50.7 | 19% | 106% | 101% | 102% |
| Jul. 03, 2008 | 50.4 | 19% | 106% | 102% | 103% |
| Jul. 04, 2008 | 55.8 | 15% | 101% | 101% | 102% |
| Jul. 05, 2008 | 56.4 | 14% | 99% | 101% | 102% |
| Jul. 06, 2008 | 55.5 | 13% | 98% | 100% | 101% |
| Jul. 07, 2008 | 55.4 | 13% | 98% | 100% | 101% |
| Jul. 08, 2008 | 55.4 | 13% | 98% | 101% | 101% |
| Jul. 09, 2008 | 55.5 | 12% | 97% | 101% | 102% |
| Jul. 10, 2008 | 55.3 | 12% | 97% | 101% | 101% |
| Jul. 11, 2008 | 55.3 | 13% | 97% | 101% | 101% |
| Jul. 12, 2008 | 55.1 | 12% | 96% | 100% | 101% |
| Jul. 13, 2008 | 55.1 | 12% | 96% | 100% | 101% |
| Jul. 14, 2008 | 55.2 | 12% | 97% | 101% | 102% |
| Jul. 15, 2008 | 55.4 | 12% | 97% | 100% | 101% |
| Jul. 16, 2008 | 53.8 | 14% | 99% | 100% | 101% |
| Jul. 17, 2008 | 53.2 | 14% | 101% | 101% | 102% |
| Jul. 18, 2008 | 53.3 | 14% | 101% | 100% | 102% |
| Jul. 19, 2008 | 53.6 | 14% | 100% | 100% | 101% |
| Jul. 20, 2008 | 53.8 | 14% | 100% | 100% | 101% |
| Jul. 21, 2008 | 53.6 | 14% | 100% | 100% | 102% |
| Jul. 22, 2008 | 53.7 | 14% | 100% | 100% | 101% |
| Jul. 23, 2008 | 53.8 | 14% | 101% | 101% | 102% |
| Jul. 24, 2008 | 53.7 | 14% | 101% | 101% | 102% |
| Jul. 25, 2008 | 56.6 | 14% | 97% | 100% | 101% |
| Jul. 26, 2008 | 56.1 | 12% | 96% | 100% | 101% |
| Jul. 27, 2008 | 56.9 | 13% | 96% | 101% | 102% |
| Jul. 28, 2008 | 55.9 | 11% | 97% | 101% | 102% |
| Jul. 29, 2008 | 54.1 | 15% | 102% | 101% | 102% |
| Jul. 30, 2008 | 52.7 | 13% | 100% | 101% | 102% |
| Jul. 31, 2008 | 56.2 | 11% | 96% | 101% | 102% |
| Aug. 01, 2008 | 54.8 | 11% | 96% | 101% | 102% |
| Aug. 02, 2008 | 54.5 | 11% | 95% | 101% | 101% |
| Aug. 03, 2008 | 54.6 | 11% | 95% | 101% | 102% |
| Aug. 04, 2008 | 55.3 | 11% | 95% | 101% | 102% |
| Aug. 05, 2008 | 55.9 | 10% | 95% | 101% | 102% |
| Aug. 06, 2008 | 56.1 | 10% | 95% | 101% | 101% |
| Aug. 07, 2008 | 56.0 | 10% | 95% | 101% | 102% |
| Aug. 08, 2008 | 55.3 | 10% | 95% | 101% | 102% |
| Aug. 09, 2008 | 55.3 | 10% | 94% | 100% | 102% |
| Aug. 10, 2008 | 55.5 | 10% | 94% | 100% | 101% |
| Aug. 11, 2008 | 54.3 | 11% | 95% | 101% | 102% |
| Aug. 12, 2008 | 53.7 | 11% | 96% | 101% | 102% |
| Aug. 13, 2008 | 53.6 | 11% | 96% | 101% | 102% |
| Aug. 14, 2008 | 53.6 | 11% | 96% | 101% | 102% |
| Aug. 15, 2008 | 53.6 | 11% | 96% | 102% | 102% |
| Aug. 16, 2008 | 53.6 | 10% | 96% | 101% | 102% |
| Aug. 17, 2008 | 53.6 | 10% | 95% | 101% | 102% |
| Aug. 18, 2008 | 53.7 | 10% | 95% | 101% | 102% |
| Aug. 19, 2008 | 53.6 | 10% | 95% | 102% | 102% |
| Aug. 20, 2008 | 53.0 | 10% | 95% | 101% | 102% |
| Aug. 21, 2008 | 46.5 | 12% | 102% | 101% | 102% |
| Aug. 22, 2008 | 44.5 | 11% | 94% | 101% | 103% |
| Aug. 23, 2008 | 43.4 | 10% | 95% | 103% | 104% |
| Aug. 24, 2008 | 43.8 | 11% | 95% | 102% | 104% |
| Aug. 25, 2008 | 44.3 | 13% | 101% | 103% | 104% |
| Aug. 26, 2008 | 49.2 | 12% | 103% | 102% | 103% |
| Aug. 27, 2008 | 49.2 | 12% | 102% | 101% | 103% |
| Aug. 28, 2008 | 48.6 | 11% | 96% | 102% | 103% |
| Sep. 14, 2008 | 42.0 | 13% | 107% | 103% | 104% |
| Sep. 15, 2008 | 40.4 | 17% | 112% | 109% | 110% |
| Sep. 16, 2008 | 46.6 | 13% | 108% | 105% | 106% |
| Sep. 17, 2008 | 48.1 | 13% | 106% | 104% | 104% |
| Sep. 18, 2008 | 48.1 | 14% | 106% | 103% | 104% |
| Sep. 19, 2008 | 48.0 | 12% | 104% | 102% | 103% |
| Sep. 20, 2008 | 47.6 | 12% | 104% | 104% | 105% |
| Sep. 21, 2008 | 47.9 | 11% | 103% | 103% | 104% |
| Sep. 22, 2008 | 48.0 | 12% | 104% | 104% | 105% |
| Sep. 23, 2008 | 56.0 | 9% | 96% | 102% | 103% |
| Sep. 24, 2008 | 55.6 | 7% | 91% | 102% | 103% |
| Sep. 25, 2008 | 55.7 | 8% | 90% | 102% | 103% |
| Sep. 26, 2008 | 55.6 | 7% | 89% | 101% | 102% |
| Sep. 27, 2008 | 55.6 | 7% | 88% | 101% | 102% |
| Sep. 28, 2008 | 55.8 | 7% | 87% | 101% | 103% |
| Sep. 29, 2008 | 54.3 | 8% | 90% | 101% | 103% |
| Sep. 30, 2008 | 56.4 | 7% | 87% | 100% | 102% |
| Oct. 01, 2008 | 57.2 | 6% | 86% | 101% | 102% |
| Oct. 02, 2008 | 57.1 | 6% | 85% | 100% | 102% |
| Oct. 03, 2008 | 56.6 | 6% | 86% | 100% | 101% |
| Oct. 04, 2008 | 56.4 | 7% | 87% | 100% | 102% |
| Oct. 05, 2008 | 55.6 | 7% | 89% | 100% | 102% |
| Oct. 06, 2008 | 56.5 | 7% | 87% | 100% | 101% |
| Oct. 07, 2008 | 57.6 | 7% | 84% | 100% | 101% |
| Oct. 08, 2008 | 57.0 | 6% | 82% | 100% | 102% |
| Oct. 09, 2008 | 56.7 | 6% | 82% | 101% | 103% |
| Oct. 10, 2008 | 55.8 | 6% | 83% | 101% | 102% |
| Oct. 11, 2008 | 55.7 | 6% | 82% | 101% | 102% |
| Oct. 12, 2008 | 55.8 | 6% | 82% | 101% | 103% |
| Oct. 13, 2008 | 55.4 | 5% | 84% | 100% | 103% |
| Oct. 14, 2008 | 56.2 | 6% | 85% | 100% | 102% |
| Oct. 15, 2008 | 56.1 | 6% | 83% | 100% | 102% |
| Oct. 16, 2008 | 55.8 | 6% | 83% | 100% | 102% |
| Oct. 17, 2008 | 55.8 | 6% | 83% | 101% | 103% |
| Oct. 18, 2008 | 55.8 | 6% | 83% | 102% | 103% |

TABLE 1-continued

Preliminary Alkylation Reactor Data

| Date | Overall temp rise ° F. | TW #1 temp rise | TW #2 temp rise | TW #3 temp rise | TW #4 temp rise |
|---|---|---|---|---|---|
| Oct. 19, 2008 | 55.9 | 6% | 82% | 102% | 103% |
| Oct. 20, 2008 | 55.5 | 5% | 82% | 101% | 102% |
| Oct. 21, 2008 | 55.4 | 5% | 85% | 101% | 103% |
| Oct. 22, 2008 | 55.5 | 6% | 85% | 102% | 103% |
| Oct. 23, 2008 | 54.9 | 5% | 85% | 102% | 104% |
| Oct. 24, 2008 | 55.0 | 5% | 84% | 101% | 103% |
| Oct. 25, 2008 | 54.9 | 5% | 84% | 102% | 103% |
| Oct. 26, 2008 | 55.3 | 5% | 80% | 101% | 103% |
| Oct. 27, 2008 | 54.1 | 5% | 81% | 102% | 104% |
| Oct. 28, 2008 | 52.4 | 7% | 94% | 103% | 105% |
| Oct. 29, 2008 | 53.6 | 4% | 81% | 101% | 103% |
| Oct. 30, 2008 | 56.0 | 5% | 76% | 101% | 103% |
| Oct. 31, 2008 | 54.4 | 5% | 75% | 100% | 102% |
| Nov. 01, 2008 | 54.3 | 5% | 75% | 101% | 103% |
| Nov. 02, 2008 | 54.4 | 5% | 75% | 100% | 103% |
| Nov. 03, 2008 | 54.5 | 5% | 76% | 100% | 102% |
| Nov. 04, 2008 | 55.1 | 5% | 75% | 101% | 103% |
| Nov. 05, 2008 | 55.6 | 5% | 74% | 100% | 102% |
| Nov. 06, 2008 | 55.5 | 5% | 75% | 100% | 102% |
| Nov. 07, 2008 | 55.3 | 5% | 75% | 101% | 103% |
| Nov. 08, 2008 | 55.4 | 5% | 76% | 101% | 102% |
| Nov. 09, 2008 | 55.1 | 5% | 76% | 101% | 103% |
| Nov. 10, 2008 | 55.6 | 5% | 75% | 101% | 103% |
| Nov. 11, 2008 | 55.2 | 5% | 76% | 100% | 102% |
| Nov. 12, 2008 | 54.6 | 5% | 78% | 101% | 103% |
| Nov. 13, 2008 | 55.0 | 5% | 77% | 100% | 103% |
| Nov. 14, 2008 | 54.7 | 5% | 78% | 101% | 103% |
| Nov. 15, 2008 | 54.5 | 4% | 77% | 102% | 104% |
| Nov. 16, 2008 | 53.5 | 4% | 76% | 102% | 104% |
| Nov. 17, 2008 | 52.8 | 4% | 76% | 101% | 103% |
| Nov. 18, 2008 | 53.9 | 4% | 75% | 102% | 104% |
| Nov. 19, 2008 | 53.4 | 4% | 75% | 102% | 103% |
| Nov. 20, 2008 | 53.2 | 4% | 75% | 102% | 104% |
| Nov. 21, 2008 | 52.5 | 4% | 75% | 103% | 105% |
| Nov. 22, 2008 | 52.9 | 5% | 76% | 102% | 104% |
| Nov. 23, 2008 | 53.5 | 4% | 75% | 101% | 103% |
| Nov. 24, 2008 | 52.8 | 4% | 75% | 101% | 103% |
| Nov. 25, 2008 | 52.8 | 4% | 75% | 102% | 104% |
| Nov. 26, 2008 | 52.7 | 4% | 74% | 101% | 103% |
| Nov. 27, 2008 | 51.9 | 4% | 73% | 101% | 102% |
| Nov. 28, 2008 | 52.3 | 4% | 73% | 101% | 102% |
| Nov. 29, 2008 | 52.5 | 5% | 73% | 101% | 103% |
| Nov. 30, 2008 | 52.2 | 4% | 73% | 102% | 104% |
| Dec. 01, 2008 | 52.8 | 4% | 73% | 102% | 104% |
| Dec. 02, 2008 | 51.3 | 4% | 76% | 102% | 104% |
| Dec. 03, 2008 | 50.9 | 5% | 76% | 101% | 103% |
| Dec. 04, 2008 | 49.6 | 5% | 78% | 104% | 105% |
| Dec. 05, 2008 | 47.8 | 5% | 80% | 104% | 105% |
| Dec. 06, 2008 | 46.3 | 5% | 81% | 103% | 105% |
| Dec. 07, 2008 | 46.0 | 5% | 81% | 103% | 105% |
| Dec. 08, 2008 | 46.5 | 6% | 80% | 102% | 103% |
| Dec. 09, 2008 | 46.5 | 5% | 80% | 102% | 104% |
| Dec. 10, 2008 | 47.0 | 5% | 82% | 104% | 106% |
| Dec. 11, 2008 | 46.3 | 5% | 82% | 104% | 107% |
| Dec. 12, 2008 | 46.0 | 5% | 82% | 103% | 105% |
| Dec. 13, 2008 | 46.3 | 5% | 82% | 102% | 104% |
| Dec. 14, 2008 | 45.6 | 6% | 87% | 102% | 105% |
| Dec. 15, 2008 | 42.6 | 8% | 99% | 103% | 105% |
| Dec. 16, 2008 | 42.8 | 8% | 105% | 104% | 105% |
| Dec. 17, 2008 | 45.0 | 8% | 102% | 103% | 103% |
| Dec. 18, 2008 | 48.9 | 5% | 81% | 101% | 102% |
| Dec. 19, 2008 | 49.5 | 5% | 74% | 101% | 103% |
| Dec. 20, 2008 | 49.7 | 5% | 72% | 101% | 103% |
| Dec. 21, 2008 | 48.1 | 4% | 73% | 103% | 105% |
| Dec. 22, 2008 | 49.7 | 4% | 74% | 103% | 106% |
| Dec. 23, 2008 | 51.2 | 4% | 73% | 101% | 103% |
| Dec. 24, 2008 | 51.2 | 4% | 72% | 100% | 103% |
| Dec. 25, 2008 | 50.6 | 5% | 75% | 101% | 103% |
| Dec. 26, 2008 | 50.3 | 6% | 80% | 101% | 102% |
| Dec. 27, 2008 | 50.1 | 5% | 80% | 101% | 103% |
| Dec. 28, 2008 | 49.9 | 5% | 81% | 103% | 104% |
| Dec. 29, 2008 | 51.2 | 6% | 82% | 102% | 103% |
| Dec. 30, 2008 | 46.0 | 5% | 82% | 98% | 100% |
| Dec. 31, 2008 | 50.8 | 6% | 78% | 102% | 104% |
| Jan. 01, 2009 | 49.9 | 5% | 82% | 102% | 104% |
| Jan. 02, 2009 | 50.0 | 5% | 82% | 102% | 103% |
| Jan. 03, 2009 | 50.5 | 5% | 82% | 102% | 103% |
| Jan. 04, 2009 | 50.1 | 5% | 82% | 101% | 102% |
| Jan. 05, 2009 | 50.0 | 5% | 81% | 101% | 103% |
| Jan. 06, 2009 | 50.0 | 5% | 82% | 102% | 104% |
| Jan. 07, 2009 | 49.9 | 5% | 82% | 103% | 104% |
| Jan. 08, 2009 | 49.8 | 5% | 82% | 102% | 103% |
| Jan. 09, 2009 | 54.0 | 3% | 73% | 101% | 102% |
| Jan. 10, 2009 | 54.7 | 4% | 71% | 101% | 103% |
| Jan. 11, 2009 | 52.0 | 5% | 79% | 103% | 105% |
| Jan. 12, 2009 | 45.8 | 6% | 94% | 105% | 105% |
| Jan. 13, 2009 | 54.4 | 4% | 75% | 102% | 105% |
| Jan. 14, 2009 | 54.5 | 4% | 74% | 102% | 103% |
| Jan. 15, 2009 | 54.2 | 4% | 74% | 103% | 105% |
| Jan. 16, 2009 | 55.1 | 4% | 73% | 103% | 105% |
| Jan. 17, 2009 | 55.8 | 4% | 71% | 101% | 104% |
| Jan. 18, 2009 | 55.4 | 4% | 71% | 101% | 103% |
| Jan. 19, 2009 | 55.7 | 4% | 72% | 102% | 103% |
| Jan. 20, 2009 | 55.8 | 4% | 70% | 102% | 105% |
| Jan. 21, 2009 | 55.5 | 4% | 69% | 101% | 103% |
| Jan. 22, 2009 | 55.8 | 4% | 70% | 101% | 103% |
| Jan. 23, 2009 | 56.1 | 4% | 69% | 101% | 102% |
| Jan. 24, 2009 | 56.5 | 4% | 69% | 101% | 103% |
| Jan. 25, 2009 | 56.6 | 4% | 69% | 101% | 103% |
| Jan. 26, 2009 | 56.9 | 4% | 69% | 100% | 102% |
| Jan. 27, 2009 | 56.7 | 4% | 70% | 100% | 102% |
| Jan. 28, 2009 | 57.1 | 3% | 69% | 101% | 104% |
| Jan. 29, 2009 | 56.9 | 4% | 68% | 102% | 104% |
| Jan. 30, 2009 | 57.2 | 4% | 68% | 101% | 103% |
| Jan. 31, 2009 | 56.9 | 4% | 67% | 101% | 103% |
| Feb. 01, 2009 | 56.8 | 4% | 67% | 100% | 103% |
| Feb. 02, 2009 | 55.2 | 4% | 67% | 102% | 104% |
| Feb. 03, 2009 | 55.1 | 4% | 66% | 101% | 103% |
| Feb. 04, 2009 | 54.0 | 4% | 67% | 102% | 105% |
| Feb. 05, 2009 | 54.3 | 4% | 70% | 101% | 103% |
| Feb. 06, 2009 | 54.6 | 4% | 66% | 100% | 103% |
| Feb. 07, 2009 | 54.6 | 4% | 64% | 100% | 102% |
| Feb. 08, 2009 | 54.4 | 4% | 63% | 100% | 103% |
| Feb. 09, 2009 | 54.7 | 4% | 63% | 100% | 102% |
| Feb. 10, 2009 | 54.8 | 4% | 62% | 99% | 102% |
| Feb. 11, 2009 | 54.6 | 4% | 62% | 100% | 102% |
| Feb. 12, 2009 | 55.0 | 4% | 62% | 100% | 102% |
| Feb. 13, 2009 | 55.0 | 3% | 61% | 100% | 102% |
| Feb. 14, 2009 | 55.0 | 4% | 62% | 100% | 103% |
| Feb. 15, 2009 | 55.1 | 4% | 61% | 101% | 103% |
| Feb. 16, 2009 | 55.2 | 4% | 61% | 100% | 103% |
| Feb. 17, 2009 | 55.2 | 4% | 61% | 100% | 102% |
| Feb. 18, 2009 | 55.3 | 4% | 60% | 100% | 102% |
| Feb. 19, 2009 | 55.0 | 4% | 60% | 101% | 104% |
| Feb. 20, 2009 | 55.2 | 3% | 60% | 100% | 103% |
| Feb. 21, 2009 | 55.2 | 4% | 59% | 100% | 103% |
| Feb. 22, 2009 | 55.2 | 4% | 59% | 101% | 104% |
| Feb. 23, 2009 | 55.1 | 4% | 59% | 100% | 104% |
| Feb. 24, 2009 | 55.5 | 4% | 58% | 99% | 103% |
| Feb. 25, 2009 | 55.4 | 3% | 57% | 99% | 101% |
| Feb. 26, 2009 | 55.1 | 3% | 57% | 99% | 102% |
| Feb. 27, 2009 | 53.0 | 4% | 60% | 100% | 102% |
| Feb. 28, 2009 | 52.6 | 4% | 61% | 101% | 105% |
| Mar. 01, 2009 | 52.5 | 4% | 58% | 101% | 105% |
| Mar. 01, 2009 | 52.5 | 4% | 58% | 101% | 105% |
| Mar. 02, 2009 | 55.0 | 3% | 57% | 100% | 104% |
| Mar. 03, 2009 | 54.4 | 4% | 56% | 100% | 103% |
| Mar. 04, 2009 | 56.0 | 4% | 58% | 99% | 102% |
| Mar. 05, 2009 | 55.7 | 4% | 59% | 100% | 102% |
| Mar. 06, 2009 | 56.6 | 4% | 57% | 99% | 102% |
| Mar. 07, 2009 | 56.3 | 4% | 56% | 99% | 102% |
| Mar. 08, 2009 | 56.3 | 3% | 56% | 98% | 102% |
| Mar. 09, 2009 | 56.0 | 4% | 55% | 99% | 102% |
| Mar. 10, 2009 | 56.4 | 4% | 54% | 99% | 102% |
| Mar. 11, 2009 | 56.4 | 4% | 54% | 98% | 102% |
| Mar. 12, 2009 | 56.3 | 4% | 54% | 99% | 103% |
| Mar. 13, 2009 | 55.6 | 3% | 53% | 99% | 103% |
| Mar. 14, 2009 | 55.9 | 4% | 53% | 99% | 103% |

TABLE 1-continued

Preliminary Alkylation Reactor Data

| Date | Overall temp rise ° F. | TW #1 temp rise | TW #2 temp rise | TW #3 temp rise | TW #4 temp rise |
| --- | --- | --- | --- | --- | --- |
| Mar. 15, 2009 | 55.6 | 3% | 53% | 99% | 102% |
| Mar. 16, 2009 | 56.0 | 3% | 53% | 99% | 103% |
| Mar. 17, 2009 | 55.9 | 4% | 53% | 99% | 102% |
| Mar. 18, 2009 | 55.9 | 3% | 53% | 99% | 102% |
| Mar. 19, 2009 | 55.6 | 3% | 52% | 98% | 102% |
| Mar. 20, 2009 | 55.5 | 4% | 52% | 99% | 103% |
| Mar. 21, 2009 | 56.2 | 4% | 52% | 98% | 102% |
| Mar. 22, 2009 | 56.6 | 3% | 53% | 98% | 102% |
| Mar. 23, 2009 | 56.7 | 4% | 52% | 98% | 102% |
| Mar. 24, 2009 | 56.4 | 4% | 52% | 98% | 101% |
| Mar. 25, 2009 | 57.3 | 3% | 50% | 98% | 101% |
| Mar. 26, 2009 | 45.8 | 8% | 55% | 101% | 105% |
| Mar. 27, 2009 | 56.3 | 3% | 53% | 99% | 102% |
| Mar. 28, 2009 | 56.6 | 3% | 52% | 98% | 104% |
| Mar. 29, 2009 | 56.1 | 4% | 53% | 100% | 103% |
| Mar. 30, 2009 | 56.4 | 3% | 52% | 99% | 102% |
| Mar. 31, 2009 | 57.3 | 3% | 47% | 97% | 102% |
| Apr. 01, 2009 | 57.0 | 3% | 48% | 98% | 102% |
| Apr. 02, 2009 | 56.9 | 3% | 48% | 97% | 102% |
| Apr. 03, 2009 | 56.3 | 3% | 49% | 98% | 102% |
| Apr. 04, 2009 | 57.1 | 3% | 47% | 96% | 101% |
| Apr. 05, 2009 | 57.1 | 2% | 46% | 97% | 102% |
| Apr. 06, 2009 | 56.9 | 3% | 47% | 98% | 104% |
| Apr. 07, 2009 | 57.0 | 2% | 47% | 98% | 103% |
| Apr. 08, 2009 | 57.4 | 3% | 48% | 98% | 102% |
| Apr. 09, 2009 | 57.1 | 4% | 50% | 99% | 102% |
| Apr. 10, 2009 | 57.3 | 3% | 47% | 97% | 101% |
| Apr. 11, 2009 | 57.2 | 4% | 47% | 98% | 103% |
| Apr. 12, 2009 | 57.1 | 3% | 47% | 98% | 102% |
| Apr. 13, 2009 | 57.1 | 3% | 46% | 97% | 102% |
| Apr. 14, 2009 | 57.1 | 4% | 47% | 98% | 103% |
| Apr. 15, 2009 | 57.0 | 4% | 46% | 98% | 102% |
| Apr. 16, 2009 | 57.1 | 4% | 46% | 98% | 102% |
| Apr. 17, 2009 | 57.3 | 3% | 46% | 98% | 102% |
| Apr. 18, 2009 | 57.3 | 3% | 46% | 97% | 102% |
| Apr. 19, 2009 | 57.1 | 3% | 45% | 97% | 102% |
| Apr. 20, 2009 | 56.9 | 4% | 46% | 97% | 103% |
| Apr. 21, 2009 | 57.0 | 3% | 45% | 97% | 102% |
| Apr. 22, 2009 | 57.0 | 3% | 45% | 97% | 101% |
| Apr. 23, 2009 | 57.0 | 3% | 45% | 97% | 101% |
| Apr. 24, 2009 | 57.2 | 3% | 45% | 97% | 102% |
| Apr. 25, 2009 | 57.2 | 4% | 45% | 97% | 102% |
| Apr. 26, 2009 | 57.2 | 3% | 44% | 96% | 101% |
| Apr. 27, 2009 | 57.4 | 4% | 45% | 97% | 101% |
| Apr. 28, 2009 | 57.4 | 3% | 44% | 97% | 102% |
| Apr. 29, 2009 | 57.5 | 4% | 44% | 97% | 101% |
| Apr. 30, 2009 | 57.0 | 3% | 44% | 96% | 101% |
| May 01, 2009 | 57.2 | 3% | 44% | 97% | 101% |
| May 02, 2009 | 57.5 | 3% | 45% | 97% | 101% |
| May 03, 2009 | 57.1 | 3% | 45% | 98% | 102% |
| May 04, 2009 | 57.3 | 3% | 44% | 97% | 102% |
| May 05, 2009 | 57.3 | 3% | 43% | 96% | 101% |
| May 06, 2009 | 57.5 | 3% | 43% | 97% | 101% |
| May 07, 2009 | 57.9 | 3% | 43% | 97% | 101% |
| May 08, 2009 | 57.8 | 3% | 43% | 96% | 101% |
| May 09, 2009 | 57.9 | 3% | 43% | 96% | 101% |
| May 10, 2009 | 57.8 | 3% | 43% | 97% | 101% |
| May 11, 2009 | 57.8 | 3% | 42% | 96% | 101% |
| May 12, 2009 | 57.9 | 3% | 42% | 96% | 101% |
| May 13, 2009 | 58.1 | 3% | 42% | 96% | 101% |
| May 14, 2009 | 57.9 | 4% | 43% | 96% | 101% |
| May 15, 2009 | 57.5 | 3% | 43% | 96% | 101% |
| May 16, 2009 | 57.1 | 3% | 42% | 96% | 102% |
| May 17, 2009 | 57.0 | 3% | 42% | 97% | 102% |
| May 18, 2009 | 56.9 | 2% | 41% | 97% | 102% |
| May 19, 2009 | 56.8 | 2% | 41% | 97% | 102% |
| May 20, 2009 | 57.2 | 2% | 41% | 96% | 101% |
| May 21, 2009 | 57.0 | 2% | 41% | 96% | 102% |
| May 22, 2009 | 57.0 | 2% | 40% | 96% | 102% |
| May 23, 2009 | 57.1 | 3% | 40% | 95% | 101% |
| May 24, 2009 | 57.2 | 2% | 39% | 95% | 101% |
| May 25, 2009 | 57.0 | 2% | 39% | 95% | 101% |
| May 26, 2009 | 57.0 | 2% | 40% | 95% | 101% |
| May 27, 2009 | 57.2 | 3% | 40% | 96% | 101% |
| May 28, 2009 | 57.2 | 3% | 40% | 95% | 101% |
| May 29, 2009 | 57.2 | 3% | 40% | 96% | 102% |
| May 30, 2009 | 57.8 | 3% | 39% | 95% | 101% |
| May 31, 2009 | 57.3 | 2% | 39% | 95% | 101% |
| Jun. 01, 2009 | 57.6 | 2% | 39% | 95% | 101% |
| Jun. 02, 2009 | 57.6 | 2% | 39% | 95% | 101% |
| Jun. 03, 2009 | 57.4 | 3% | 38% | 95% | 101% |
| Jun. 04, 2009 | 57.1 | 3% | 38% | 95% | 102% |
| Jun. 05, 2009 | 56.7 | 3% | 40% | 96% | 102% |
| Jun. 06, 2009 | 56.8 | 3% | 41% | 96% | 101% |
| Jun. 07, 2009 | 57.1 | 3% | 38% | 95% | 101% |
| Jun. 07, 2009 | 57.1 | 3% | 38% | 95% | 101% |
| Jun. 08, 2009 | 57.2 | 2% | 38% | 95% | 100% |
| Jun. 09, 2009 | 57.2 | 2% | 37% | 94% | 100% |
| Jun. 10, 2009 | 57.3 | 3% | 37% | 95% | 100% |
| Jun. 11, 2009 | 57.1 | 2% | 37% | 95% | 100% |
| Jun. 12, 2009 | 57.2 | 2% | 37% | 95% | 100% |
| Jun. 13, 2009 | 57.1 | 2% | 37% | 95% | 100% |
| Jun. 14, 2009 | 57.4 | 2% | 36% | 94% | 100% |
| Jun. 15, 2009 | 57.2 | 2% | 36% | 95% | 100% |
| Jun. 16, 2009 | 57.4 | 3% | 36% | 94% | 100% |
| Jun. 17, 2009 | 57.2 | 2% | 36% | 94% | 101% |
| Jun. 18, 2009 | 57.1 | 2% | 36% | 94% | 101% |
| Jun. 19, 2009 | 57.2 | 3% | 36% | 94% | 101% |
| Jun. 20, 2009 | 57.4 | 3% | 36% | 94% | 100% |
| Jun. 21, 2009 | 57.1 | 2% | 36% | 94% | 100% |
| Jun. 22, 2009 | 56.9 | 2% | 35% | 94% | 101% |
| Jun. 23, 2009 | 57.1 | 2% | 35% | 94% | 100% |
| Jun. 24, 2009 | 56.8 | 3% | 35% | 94% | 101% |
| Jun. 25, 2009 | 56.9 | 3% | 35% | 94% | 100% |
| Jun. 26, 2009 | 57.0 | 3% | 35% | 94% | 101% |
| Jun. 27, 2009 | 56.9 | 2% | 34% | 94% | 100% |
| Jun. 28, 2009 | 56.8 | 2% | 34% | 94% | 101% |
| Jun. 29, 2009 | 57.1 | 3% | 34% | 94% | 101% |
| Jun. 30, 2009 | 56.9 | 2% | 34% | 94% | 100% |
| Jul. 01, 2009 | 56.9 | 3% | 34% | 94% | 101% |
| Jul. 02, 2009 | 57.0 | 2% | 34% | 93% | 100% |
| Jul. 03, 2009 | 57.1 | 2% | 34% | 93% | 100% |
| Jul. 04, 2009 | 56.9 | 2% | 33% | 93% | 100% |
| Jul. 05, 2009 | 56.8 | 2% | 33% | 93% | 100% |
| Jul. 06, 2009 | 57.0 | 2% | 33% | 94% | 101% |
| Jul. 07, 2009 | 57.0 | 3% | 33% | 94% | 101% |
| Jul. 08, 2009 | 56.8 | 2% | 33% | 93% | 101% |
| Jul. 09, 2009 | 50.4 | 3% | 46% | 98% | 102% |
| Jul. 10, 2009 | 49.7 | 3% | 50% | 100% | 102% |
| Jul. 11, 2009 | 53.1 | 3% | 37% | 95% | 101% |
| Jul. 12, 2009 | 57.0 | 2% | 31% | 92% | 100% |
| Jul. 13, 2009 | 56.7 | 2% | 30% | 92% | 100% |
| Jul. 14, 2009 | 56.9 | 2% | 30% | 92% | 100% |
| Jul. 15, 2009 | 57.1 | 3% | 30% | 92% | 100% |
| Jul. 16, 2009 | 57.1 | 3% | 30% | 93% | 100% |
| Jul. 17, 2009 | 56.9 | 2% | 30% | 92% | 101% |
| Jul. 18, 2009 | 57.2 | 2% | 30% | 92% | 101% |
| Jul. 19, 2009 | 57.0 | 2% | 30% | 92% | 101% |
| Jul. 20, 2009 | 56.9 | 2% | 30% | 92% | 101% |
| Jul. 21, 2009 | 57.0 | 3% | 30% | 93% | 101% |
| Jul. 22, 2009 | 57.0 | 2% | 30% | 93% | 100% |
| Jul. 23, 2009 | 56.8 | 3% | 30% | 93% | 101% |
| Jul. 24, 2009 | 56.7 | 3% | 30% | 92% | 101% |
| Jul. 25, 2009 | 56.8 | 3% | 29% | 92% | 100% |
| Jul. 26, 2009 | 56.9 | 3% | 29% | 92% | 101% |
| Jul. 27, 2009 | 56.2 | 3% | 30% | 93% | 101% |
| Jul. 28, 2009 | 54.4 | 2% | 31% | 94% | 101% |
| Jul. 29, 2009 | 56.9 | 3% | 29% | 92% | 100% |
| Jul. 30, 2009 | 57.0 | 2% | 28% | 92% | 100% |
| Jul. 31, 2009 | 56.8 | 2% | 29% | 91% | 100% |
| Aug. 01, 2009 | 57.3 | 3% | 29% | 92% | 100% |
| Aug. 02, 2009 | 57.5 | 2% | 28% | 91% | 100% |
| Aug. 03, 2009 | 57.5 | 3% | 28% | 91% | 100% |
| Aug. 04, 2009 | 57.4 | 2% | 28% | 91% | 100% |
| Aug. 05, 2009 | 56.5 | 2% | 28% | 91% | 100% |
| Aug. 06, 2009 | 56.9 | 2% | 28% | 91% | 101% |
| Aug. 07, 2009 | 57.2 | 2% | 28% | 91% | 101% |
| Aug. 08, 2009 | 57.2 | 2% | 28% | 91% | 100% |

TABLE 1-continued

Preliminary Alkylation Reactor Data

| Date | Overall temp rise ° F. | TW #1 temp rise | TW #2 temp rise | TW #3 temp rise | TW #4 temp rise |
|---|---|---|---|---|---|
| Aug. 09, 2009 | 57.3 | 3% | 28% | 90% | 100% |
| Aug. 10, 2009 | 57.1 | 2% | 27% | 90% | 100% |
| Aug. 11, 2009 | 57.3 | 2% | 26% | 90% | 100% |
| Aug. 12, 2009 | 57.4 | 2% | 28% | 91% | 100% |
| Aug. 13, 2009 | 57.3 | 3% | 31% | 93% | 101% |
| Aug. 14, 2009 | 57.2 | 2% | 27% | 91% | 101% |
| Aug. 15, 2009 | 57.8 | 3% | 26% | 90% | 100% |
| Aug. 16, 2009 | 57.6 | 2% | 26% | 90% | 100% |
| Aug. 17, 2009 | 57.5 | 3% | 27% | 91% | 100% |
| Aug. 18, 2009 | 57.3 | 3% | 26% | 90% | 100% |
| Aug. 19, 2009 | 57.4 | 3% | 26% | 90% | 100% |
| Aug. 20, 2009 | 57.5 | 2% | 25% | 89% | 100% |
| Aug. 21, 2009 | 56.5 | 2% | 26% | 91% | 101% |
| Aug. 22, 2009 | 57.6 | 3% | 26% | 90% | 101% |
| Aug. 23, 2009 | 57.4 | 2% | 26% | 91% | 101% |
| Aug. 24, 2009 | 57.7 | 3% | 25% | 90% | 101% |
| Aug. 25, 2009 | 57.6 | 3% | 24% | 89% | 100% |
| Aug. 26, 2009 | 57.8 | 3% | 24% | 88% | 100% |
| Aug. 27, 2009 | 57.6 | 2% | 24% | 88% | 100% |
| Aug. 28, 2009 | 57.7 | 3% | 24% | 88% | 100% |
| Aug. 29, 2009 | 57.9 | 3% | 23% | 88% | 100% |
| Aug. 30, 2009 | 57.7 | 3% | 24% | 88% | 101% |
| Aug. 31, 2009 | 55.0 | 3% | 24% | 88% | 100% |
| Sep. 01, 2009 | 57.6 | 2% | 25% | 90% | 102% |
| Sep. 02, 2009 | 57.8 | 3% | 23% | 88% | 101% |
| Sep. 03, 2009 | 57.7 | 3% | 23% | 88% | 101% |
| Sep. 04, 2009 | 57.4 | 2% | 23% | 88% | 100% |
| Sep. 05, 2009 | 57.2 | 2% | 23% | 88% | 100% |
| Sep. 06, 2009 | 57.3 | 2% | 23% | 88% | 100% |
| Sep. 07, 2009 | 57.3 | 2% | 23% | 87% | 100% |
| Sep. 08, 2009 | 57.4 | 3% | 22% | 87% | 100% |
| Sep. 09, 2009 | 57.4 | 3% | 22% | 86% | 100% |
| Sep. 10, 2009 | 57.3 | 2% | 21% | 86% | 100% |
| Sep. 11, 2009 | 57.4 | 3% | 21% | 86% | 100% |
| Sep. 12, 2009 | 57.5 | 3% | 21% | 86% | 100% |
| Sep. 13, 2009 | 57.5 | 3% | 21% | 85% | 100% |

Various terms are used herein, to the extent a term used in not defined herein, it should be given the broadest definition persons in the pertinent art have given that term as reflected in printed publications and issued patents.

The term "activity" refers to the weight of product produced per weight of the catalyst used in a process per hour of reaction at a standard set of conditions (e.g., grams product/gram catalyst/hr).

The term "alkyl" refers to a functional group or side-chain that consists solely of single-bonded carbon and hydrogen atoms, for example a methyl or ethyl group.

The term "alkylation" refers to the addition of an alkyl group to another molecule.

The term "conversion" refers to the percentage of input converted.

The term "deactivated catalyst" refers to a catalyst that has lost enough catalyst activity to no longer be efficient in a specified process.

The term "high poison feed stream" refers to a feed stream that typically contains impurities that deactivate a catalyst in quantities that range from 10 ppb to 100 ppb or more and can typically average from 20 ppb to 40 ppb.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

The term "recycle" refers to returning an output of a system as input to either that same system or another system within a process. The output may be recycled to the system in any manner known to one skilled in the art, for example, by combining the output with the input stream or by directly feeding the output into the system. In addition, multiple input streams may be fed to a system in any manner known to one skilled in the art.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable level. Examples of such regeneration may include passing steam over a catalyst bed or burning off carbon residue, for example.

The term "transalkylation" refers to the transfer of an alkyl group from one aromatic molecule to another.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof.

What is claimed is:

1. A method of producing an alkylaromatic by the alkylation of an aromatic with an alkylating agent, the method comprising:
   providing at least one reaction zone containing a regenerated H-beta zeolite catalyst;
   introducing a feed stream to the reaction zone, wherein the feed stream comprises an aromatic, an alkylating agent, and catalyst poisons averaging at least 5 ppb;
   reacting at least a portion of the aromatic under alkylation conditions to produce an alkylaromatic;
   wherein the regenerated H-beta zeolite catalyst is produced by heating an at least partially deactivated H-beta zeolite catalyst to a series of temperatures ranging from about 200° C. to about 500° C., said heating comprising:
   heating the at least partially deactivated H-beta zeolite catalyst to a first temperature with a gas containing nitrogen and 2 mol % or less oxygen for a period of time for a time sufficient to provide an output stream having an oxygen content of about 0.1 mol %;
   heating up the at least partially deactivated H-beta zeolite catalyst at a second temperature higher than the first temperature for a period of time sufficient to provide an output stream having a certain oxygen content.

2. A method of producing an alkylaromatic by the alkylation of an aromatic with an alkylating agent, the method comprising:
   providing a reaction zone comprising a preliminary alkylation system containing an H-beta zeolite catalyst and an alkylation reactor containing an alkylation catalyst, wherein the alkylation reactor is in fluid communication with the preliminary alkylation system, and wherein the alkylation catalyst is a catalyst other than H-beta zeolite;

introducing a feed stream to the reaction zone, wherein the feed stream comprises an aromatic, an alkylating agent, and catalyst poisons averaging at least 5 ppb;

reacting at least a portion of the aromatic under alkylation conditions to produce an alkylaromatic;

wherein at least one of the H-beta zeolite and the alkylation catalyst is regenerated by heating an at least partially deactivated catalyst to a series of temperatures ranging from about 200° C. to about 500° C., said heating comprising:

heating the at least partially deactivated H-beta zeolite catalyst to a first temperature with a gas containing nitrogen and 2 mol % or less oxygen for a period of time for a time sufficient to provide an output stream having an oxygen content of about 0.1 mol %;

heating up the at least partially deactivated H-beta zeolite catalyst at a second temperature higher than the first temperature for a period of time sufficient to provide an output stream having a certain oxygen content.

3. The method of claim 1, wherein the feed stream comprises catalyst poisons averaging at least 30 ppb.

4. The method of claim 1, wherein the feed stream comprises catalyst poisons averaging at least 75 ppb.

5. The method of claim 1, wherein the amount of regenerated H-beta catalyst in the at least one reaction zone is at least 3,000 pounds.

6. The method of claim 1, wherein the amount of regenerated H-beta catalyst in the at least one reaction zone is between 3,000 pounds and 50,000 pounds in a first preliminary alkylation system.

7. The method of claim 1, wherein the alkylaromatic production is at least 0.5 million pounds per day.

8. The method of claim 1, wherein the alkylaromatic is ethylbenzene, the aromatic is benzene and the alkylating agent is ethylene.

9. The method of claim 1, wherein the at least one reaction zone comprises at least one preliminary alkylation reactor and at least one primary alkylation reactor.

10. The method of claim 9, wherein the at least one preliminary alkylation reactor contains the regenerated H-beta zeolite catalyst in a quantity of between at least 3,000 pounds to 50,000 pounds.

11. The method of claim 9, wherein the preliminary alkylation reactor has a run time of at least 6 months prior to regeneration.

12. The method of claim 9, wherein the preliminary alkylation reactor has a run time of at least 12 months prior to regeneration.

13. The method of claim 9, wherein the preliminary alkylation reactor has a run time of at least 18 months prior to regeneration.

14. The method of claim 9, wherein the regenerated H-beta zeolite catalyst in the preliminary alkylation reactor can be regenerated in-situ.

15. The method of claim 9, wherein the preliminary alkylation reactor can be bypassed for catalyst regeneration without taking the at least one primary alkylation reactor out of service.

16. The method of claim 9, wherein the preliminary alkylation reactor contains a mixed catalyst that includes the regenerated H-beta zeolite catalyst and at least one other catalyst.

17. The method of claim 9, wherein the primary alkylation reactor contains a mixed catalyst that includes H-beta zeolite catalyst and at least one other catalyst.

18. The method of claim 9, wherein the primary alkylation reactor experiences a decrease in catalyst deactivation when the preliminary alkylation reactor is in service.

19. The method of claim 9, wherein the primary alkylation reactor experiences no catalyst deactivation when the preliminary alkylation reactor is in service.

20. The method of claim 1, wherein the at least one reaction zone contains a mixed catalyst that includes the regenerated H-beta zeolite catalyst and at least one other catalyst.

21. The method of claim 1, wherein the alkylaromatic is ethylbenzene, the aromatic is benzene, and the alkylating agent is ethylene;

and wherein the feed stream contains at least 10 ppb poisons.

22. The process of claim 21, wherein the regenerated H-beta catalyst has a deactivation rate of no more than 30 pounds of catalyst per million pounds of ethylbenzene produced.

23. The process of claim 21, wherein the regenerated H-beta catalyst has a deactivation rate of no more than 10 pounds of catalyst per million pounds of ethylbenzene produced.

24. The process of claim 21, wherein the regenerated H-beta catalyst has a deactivation rate of no more than 2.5 pounds of catalyst per million pounds of ethylbenzene produced.

25. The process of claim 21, wherein the amount of catalyst in the at least one reaction zone is from 3,000 to 7,000 pounds and produces over 1,000 million pounds of ethylbenzene prior to regeneration of the catalyst.

26. The process of claim 21, wherein the amount of catalyst in the at least one reaction zone is from 10,000 to 12,000 pounds and produces over 2,000 million pounds of ethylbenzene prior to regeneration of the catalyst.

27. The process of claim 21, wherein the amount of catalyst in the at least one reaction zone is from 20,000 to 22,000 pounds and produces over 4,000 million pounds of ethylbenzene prior to regeneration of the catalyst.

28. The process of claim 21, wherein the at least one reaction zone contains a mixed catalyst that includes the regenerated H-beta zeolite catalyst and at least one other catalyst.

29. The method of claim 1, wherein the alkylaromatic is ethylbenzene, the aromatic is benzene, and the alkylating agent is ethylene;

wherein the at least one reaction zone contains 20,000 to 25,000 pounds of the regenerated H-beta zeolite catalyst;

wherein the feed stream contains at least 10 ppb poisons, and wherein an average of at least 16 million pounds of benzene per day is introduced into the at least one reaction zone; and wherein ethylbenzene is produced at a rate averaging at least 7.0 million pounds per day, for a cumulative run time of 6 months to produce a total of at least 1,200 million pounds of ethylbenzene;

wherein the catalyst deactivation is less than 20% of the total regenerated H-beta zeolite catalyst charge at the end of the run.

30. The process of claim 29, wherein the at least one reaction zone contains a mixed catalyst that includes the regenerated H-beta zeolite catalyst and at least one other catalyst.

31. A method of producing an alkylaromatic by the alkylation of an aromatic with an alkylating agent, the method comprising:

providing a reaction zone comprising a preliminary alkylation system containing an H-beta zeolite catalyst, an alkylation reactor containing an alkylation catalyst, wherein the alkylation reactor is in fluid communication with the preliminary alkylation system, and wherein the alkylation catalyst is a catalyst other than H-beta zeolite and a transalkylation system in fluid communication with the alkylation reactor, wherein the transalkylation system comprises a transalkylation catalyst;

introducing a feed stream to the reaction zone, wherein the feed stream comprises an aromatic, an alkylating agent, and catalyst poisons averaging at least 5 ppb; and reacting at least a portion of the aromatic under alkylation conditions to produce an alkylaromatic;

wherein at least one of the H-beta zeolite, the alkylation catalyst, and the transalkylation catalyst is regenerated by heating an at least partially deactivated catalyst to a series of temperatures ranging from about 200° C. to about 500° C., said heating comprising:

heating the at least partially deactivated H-beta zeolite catalyst to a first temperature with a gas containing nitrogen and 2 mol % or less oxygen for a period of time for a time sufficient to provide an output stream having an oxygen content of about 0.1 mol %; and heating up the at least partially deactivated H-beta zeolite catalyst at a second temperature higher than the first temperature for a period of time sufficient to provide an output stream having a certain oxygen content.

\* \* \* \* \*